United States Patent
Hofstetter et al.

(10) Patent No.: US 11,406,361 B2
(45) Date of Patent: Aug. 9, 2022

(54) MAPPING SHEAR WAVE VELOCITY AND SHEAR MODULUS IN BIOLOGICAL TISSUES

(71) Applicants: Siemens Healthcare GmbH, Erlangen (DE); University of Utah Research Foundation, Salt Lake City, UT (US)

(72) Inventors: Lorne Hofstetter, Salt Lake City, UT (US); Bradley Drake Bolster, Jr., Sandy, UT (US); Dennis L. Parker, Centerville, UT (US); Henrik Odeen, Salt Lake City, UT (US); Allison Payne, Salt Lake City, UT (US)

(73) Assignees: Siemens Healthcare GmbH, Erlangen (DE); University of Utah Research Foundation, Salt Lake City, UT (US)

(*) Notice: Subject to any disclaimer, the term of this patent is extended or adjusted under 35 U.S.C. 154(b) by 378 days.

(21) Appl. No.: 16/442,628

(22) Filed: Jun. 17, 2019

(65) Prior Publication Data

US 2020/0008783 A1    Jan. 9, 2020

Related U.S. Application Data

(60) Provisional application No. 62/694,870, filed on Jul. 6, 2018.

(51) Int. Cl.
| | |
|---|---|
| *A61B 8/08* | (2006.01) |
| *G01S 7/52* | (2006.01) |
| *A61B 5/00* | (2006.01) |
| *G16H 30/40* | (2018.01) |

(52) U.S. Cl.
CPC ............ *A61B 8/485* (2013.01); *A61B 5/0048* (2013.01); *A61B 8/5223* (2013.01); *G01S 7/52042* (2013.01); *G16H 30/40* (2018.01)

(58) Field of Classification Search
USPC ........................................................ 600/407
See application file for complete search history.

(56) References Cited

U.S. PATENT DOCUMENTS

2013/0041249 A1* 2/2013 Salomir .................. A61N 7/02
600/411

OTHER PUBLICATIONS

Liu, Y., Fite, B. Z., Mahakian, L. M., Johnson, S. M., Larrat, B., Dumont, E., & Ferrara, K. W. (2015). Concurrent visualization of acoustic radiation force displacement and shear wave propagation with 7T MRI. PLoS One, 10(10), e0139667. (Year: 2015).*
(Continued)

*Primary Examiner* — Serkan Akar
*Assistant Examiner* — Renee C Langhals

(57) ABSTRACT

A method for mapping shear wave velocity in biological tissues includes using an ultrasound transducer to generate mechanical excitations at a plurality of locations in a region of interest. An MRI system is used to capture a phase image of each mechanical excitation, wherein motion encoding gradients (MEGs) of the MRI system encode a propagating shear wavefront caused by the mechanical excitation. A plurality of shear wave velocity maps is generated based on the phase images, wherein each shear wave velocity map depicts velocity between adjacent propagating shear wavefronts. The shear wave speed values are combined to generate a composite shear wave velocity map of the region of interest.

19 Claims, 14 Drawing Sheets

(56) References Cited

OTHER PUBLICATIONS

Larrat, B., Pernot, M., Aubry, J. F., Dervishi, E., Sinkus, R., Seilhean, D., . . . & Tanter, M. (2009). MR-guided transcranial brain HIFU in small animal models. Physics in medicine & biology, 55(2), 365. (Year: 2009).*

McDannold, N., & Maier, S. E. (2008). Magnetic resonance acoustic radiation force imaging. Medical physics, 35(8), 3748-3758. (Year: 2008).*

Auboiroux, V., Viallon, M., Roland, J., Hyacinthe, J. N., Petrusca, L., Morel, D. R., . . . & Salomir, R. (2012). ARFI-prepared MRgHIFU in liver: simultaneous mapping of ARFI-displacement and temperature elevation, using a fast GRE-EPI sequence. Magnetic resonance in medicine, 68(3), 932-946. (Year: 2012).*

Zhu, J., Qi, L., Miao, Y., Ma, T., Dai, C., Qu, Y., . . . & Chen, Z. (2016). 3D mapping of elastic modulus using shear wave optical micro-elastography. Scientific reports, 6(1), 1-9. (Year: 2016).*

Muthupillai, R., et al. "Magnetic resonance elastography by direct visualization of propagating acoustic strain waves." Science 269. 5232 (1995): 1854-1857.

Bercoff, Jérémy, Mickael Tanter, and Mathias Fink. "Supersonic shear imaging: a new technique for soft tissue elasticity mapping." IEEE transactions on ultrasonics, ferroelectrics, and frequency control 51.4 (2004): 396-409.

Sarvazyan, Armen P., et al. "Shear wave elasticity imaging: a new ultrasonic technology of medical diagnostics." Ultrasound in medicine & biology 24.9 (1998): 1419-1435.

Wu, Tao, et al. "MR imaging of shear waves generated by focused ultrasound." Magnetic Resonance in Medicine: An Official Journal of the International Society for Magnetic Resonance in Medicine 43.1 (2000): 111-115.

Liu, Yu et al. "Concurrent visualization of acoustic radiation force displacement and shear wave propagation with 7T MRI." PloS one 10.10 (2015): e0139667.

McCracken, Paul J., et al. "Mechanical transient-based magnetic resonance elastography." Magnetic Resonance in Medicine: An Official Journal of the International Society for Magnetic Resonance in Medicine 53.3 (2005): 628-639.

Souchon, Rémi, et al. "Transient MR elastography (t-MRE) using ultrasound radiation force: theory, safety, and initial experiments in vitro." Magnetic Resonance in Medicine: An Official Journal of the International Society for Magnetic Resonance in Medicine 60.4 (2008): 871-881.

Liu, Yu, et al. "Supersonic transient magnetic resonance elastography for quantitative assessment of tissue elasticity." Physics in Medicine & Biology 62.10 (2017): 4083.

de Bever, Joshua T., et al. "Simultaneous MR thermometry and acoustic radiation force imaging using interleaved acquisition." Magnetic resonance in medicine 79.3 (2018): 1515-1524.

Odéen, Henrik, et al. "Multiple-point magnetic resonance acoustic radiation force imaging." Magnetic resonance in medicine 81.2 (2019): 1104-1117.

Wu, Tao, et al. "Assessment of thermal tissue ablation with MR elastography." Magnetic Resonance in Medicine: An Official Journal of the International Society for Magnetic Resonance in Medicine 45.1 (2001): 80-87.

Arnal, Bastien, Mathieu Pernot, and Mickael Tanter. "Monitoring of thermal therapy based on shear modulus changes: II. Shear wave imaging of thermal lesions." IEEE transactions on ultrasonics, ferroelectrics, and frequency control 58.8 (2011): 1603-1611.

McDannold, Nathan, and Stephan E. Maier. "Magnetic resonance acoustic radiation force imaging." Medical physics 35.8 (2008): 3748-3758.

Vappou, Jonathan, et al. "MR-ARFI-based method for the quantitative measurement of tissue elasticity: application for monitoring HIFU therapy." Physics in Medicine & Biology 63.9 (2018): 095018.

* cited by examiner

Fig. 10

MAPPING SHEAR WAVE VELOCITY AND SHEAR MODULUS IN BIOLOGICAL TISSUES

CROSS REFERENCE TO RELATED APPLICATIONS

This application claims priority to U.S. Provisional Application Ser. No. 62/694,870 filed Jul. 6, 2018, the contents of which are incorporated by reference.

STATEMENT REGARDING FEDERALLY SPONSORED RESEARCH OR DEVELOPMENT

This invention was made with government support under grant numbers EB023712, CA172787, and CA228363 awarded by the National Institutes of Health. The government has certain rights in the invention.

TECHNICAL FIELD

The present invention relates generally to mapping shear wave velocity and shear modulus in biological tissues. The techniques described may be particularly useful at detecting diseased tissue and at assessing mechanical changes in tissue due to magnetic resonance-guided focused ultrasound therapies.

BACKGROUND

Clinicians use manual palpation to assess tissue stiffness and to evaluate and detect pathology. While palpation is widely used as part of the physical diagnosis, it is qualitative and generally limited to superficial regions. Therefore, researchers are developing and evaluating quantitative imaging approaches to noninvasively measure stiffness in both superficial and deep seated tissues.

A variety of ultrasound (US) and magnetic resonance (MR) elastography (MRE) methods have been developed to measure the shear wave speed ($c_s$) or shear modulus ($\mu$) of tissues. In an ideal elastic non-dissipative medium, the speed of a propagating shear wave is related to the shear modulus by $\mu = \rho c_s^2$, where $\rho$ is the medium density. The shear modulus provides a quantitative representation of the tissue properties that are qualitatively evaluated using manual palpation.

In many elastography techniques, a stress is applied to the tissue and the resulting dynamic tissue strain is monitored with imaging. In MRE, the induced mechanical strain is encoded in the MR image phase using motion-encoding gradients (MEGs). Mechanical excitation is typically achieved using vibratory motion from an external oscillatory driver or the acoustic radiation force (ARF) from a focused US (FUS) transducer. The use of either transient or harmonic (i.e., steady-state) excitation modes have been explored. Harmonic MRE techniques are the most developed and have been used to detect liver fibrosis and measure tissue mechanical properties in brain, breast, kidney, and heart. Elastography techniques that use the acoustic radiation force for mechanical excitation may be advantageous for certain applications. With a FUS transducer, it is possible to supply the mechanical excitation directly into the tissue of interest. Additionally, the predominant direction of the propagating shear wave is perpendicular to the FUS beam, which makes orientation of the MEG straightforward. Finally, FUS induced MRE could become an important tool for treatment planning, monitoring, and endpoint assessment in MR-guided FUS therapies. A main benefit with such techniques is that the same FUS device used for treatment can be used for elastography. However, conventional elastography methods that utilize ARF excitations and displacement encoding with MR imaging require long acquisition times and produce low resolution elastography maps.

SUMMARY

Embodiments of the present invention address and overcome one or more of the above shortcomings and drawbacks, by providing methods, systems, and apparatuses related to mapping shear wave velocity and shear modulus in biological tissues.

According to some embodiments, a method for mapping shear wave velocity in biological tissues includes using an ultrasound transducer to generate mechanical excitations at a plurality of locations in a region of interest. Such excitations may be generated, for example, using acoustic radiation force (ARF) impulses applied to the region of interest. An MRI system is used to capture a phase image of each mechanical excitation. Motion encoding gradients (MEGs) encode a propagating shear wavefront caused by the mechanical excitation. The MEGs may be, for example, trapezoidal shaped waveforms or sinusodal shaped waveforms. A plurality of shear wave velocity maps are generated based on the phase images. Each shear wave velocity map depicts velocity between adjacent propagating shear wavefronts. The shear wave speed values are combined to generate a composite shear wave velocity map of the region of interest. In some embodiments, the velocity values in the shear wave velocity maps may be further used to determine one or more shear modulus values for the region of interest.

Various enhancements, refinements, and other modifications can be made to the aforementioned method in different embodiments. For example, in some embodiments, the reference image of a region of interest is acquired without any excitation from the ultrasound transducer in the region of interest. Then, prior to generation of the shear wave velocity maps, the reference MRI image is subtracted from each phase image to minimize phase variations not caused by the mechanical excitations. In some embodiments, the MRI system further encodes a position of an initial disturbance caused by the mechanical excitation in each phase image. The position of the initial disturbance and the propagating shear wavefront may be encoded, for example, as positive and negative values in the phase image. In some embodiments, each phase image differs in spatial location of the mechanical excitations within the region of interest. In other embodiments, each phase image differs in relative timing of the mechanical excitations in the region of interest. In one embodiment, the ultrasound transducer generates the mechanical excitations using a focused ultrasound (FUS) beam and lobes of the MEGs are oriented parallel to the FUS beam. In some embodiments, the MRI system captures each phase image using a 3D gradient echo segmented echo planar imaging pulse sequence.

According to another aspect of the present invention, a system for mapping shear wave velocity in biological tissues includes an ultrasound transducer, an MRI system, and one or more computers. The ultrasound transducer generates mechanical excitations at a plurality of locations in a region of interest. The MRI system captures a phase image of each mechanical excitation. MEGs of the MRI system encode a propagating shear wavefront caused by the mechanical excitation. The computers generate a plurality of shear wave velocity maps based on the phase images, wherein each shear wave velocity map depicts velocity between adjacent propagating shear wavefronts. The computers may then combine the shear wave speed values to generate a composite shear wave velocity map of the region of interest.

In some embodiments, the MRI system is further configured to receive a reference image of a region of interest without any mechanical excitation caused by the ultrasound transducer in the region of interest. In these embodiments, the computers are further configured to, prior to generation of the shear wave velocity maps, subtract the reference MRI image from each phase image to minimize phase variations not caused by the mechanical excitations.

According to another aspect of the present invention, the aforementioned method may be adapted as an article of manufacture comprising a non-transitory, tangible computer-readable medium holding computer-executable instructions for performing a method that includes receiving a plurality of phase images of a region of interest acquired by an MRI system. As with the method discussed above, each phase image is encoded with information describing propagating shear wavefronts caused by mechanical excitation of the region of interest caused by an ultrasound transducer. A plurality of shear wave velocity maps are then generated based on the phase images. Each shear wave velocity map depicts velocity between adjacent propagating shear wavefronts. The shear wave speed values are combined to generate a composite shear wave velocity map of the region of interest. In some embodiments, the method may further include receiving a reference image of a region of interest without any mechanical excitation caused by the ultrasound transducer in the region of interest. Then, prior to generation of the shear wave velocity maps, the reference MRI image can be subtracted from each phase image to minimize phase variations unrelated to the mechanical excitations caused by the ultrasound transducer.

Additional features and advantages of the invention will be made apparent from the following detailed description of illustrative embodiments that proceeds with reference to the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing and other aspects of the present invention are best understood from the following detailed description when read in connection with the accompanying drawings. For the purpose of illustrating the invention, there are shown in the drawings embodiments that are presently preferred, it being understood, however, that the invention is not limited to the specific instrumentalities disclosed. Included in the drawings are the following Figures:

FIG. 10 provides a table with example parameters used for MR-SWE and MRE measurements;

DETAILED DESCRIPTION

The present disclosure describes systems and methods related to a rapid Magnetic Resonance Imaging (MRI)-based method of generating both 2D and volumetric shear wave speed maps from ARF generated impulses. Briefly, a multiple-point shear wave elastography (MR-SWE) is disclosed herein that leverages the electronic steering capabilities of phased-array FUS systems. MR-SWE uses a single ARF impulse followed by a motion encoding gradient (MEG) train to encode the location of the propagating shear wave packet at multiple time-points in each phase image. Leveraging the electronic steering capabilities of phased array FUS transducers and, using an interleaving scheme, phase images are acquired such that the ARF impulse spatial position for each image is different.

The benefit of the multipoint approach described herein over conventional techniques is three-fold. First, ARF induced shear wavefronts attenuate rapidly, which limits the spatial extent of the region over which the shear wave speed can be measured. By varying the ARF location, shear wave speeds over a larger volume can be achieved when measurements are combined together. Second, from overlapped regions, the propagation time between the initial ARF impulse and the next encoded wavefront can be determined. This allows the data to be more fully used; shear wave speed between initial ARF location and the first encoded wavefront can be computed if this timing is known. The third benefit over conventional techniques is that the redundant overlapping measurements can be combined to improve the precision of the measured shear wave speed. Both the efficient shear wavefront encoding scheme and acquisition of images with different ARF impulse locations generate a very rich dataset from which high-resolution shear wave speed maps can be generated. Using this new MR shear wave elastography (MR-SWE) technique, a complete acquisition of a 2D map is possible within a 12 s breath-hold.

Figure 1:
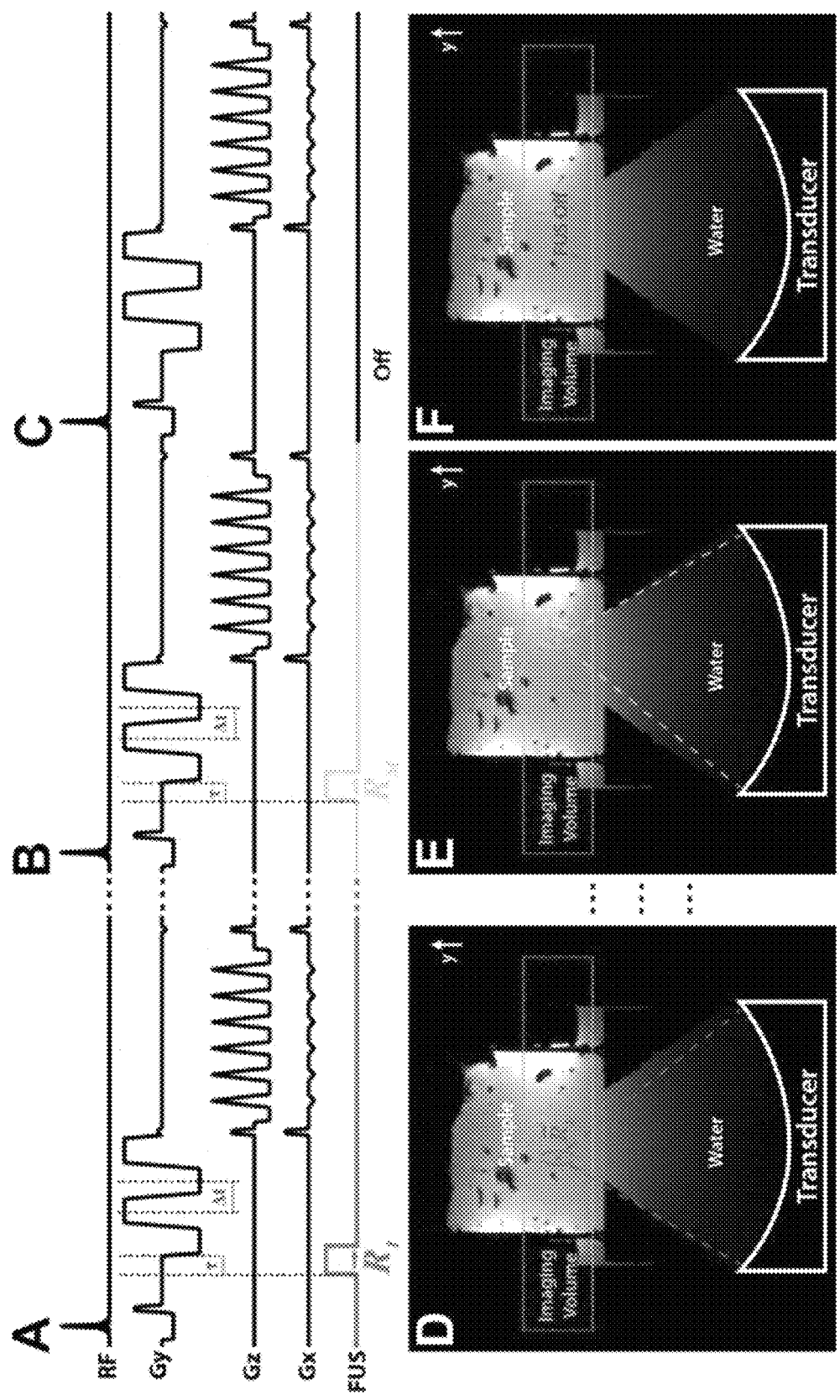
FIG. 1 shows a pulse sequence diagram (top row) for performing mapping shear wave velocity, according to the techniques described herein, and corresponding experimental setups (bottom row) used for proof of concept of the techniques.

FIG. 1 shows the components of an example MR-SWE acquisition, as it may be implemented in some embodiments. In this example, four motion encoding gradient (MEG) lobes along the FUS beam direction were added to a 3D gradient echo segmented echo planar imaging (EPI) pulse sequence. Optical triggers synchronized the short ARF pulse to start a time τ before the start of the first MEG lobe. The first MEG lobe encodes the position of the initial F impulse. Lobes 2, 3, and 4 sample the propagating shear wavefront at times (τ+3Δt/2, τ+5Δt/2, τ+7Δt/2) where Δt is the center-to-center spacing between MEG lobes. This distance between adjacent wavefront positons divided by the MEG lobe spacing (Δt) provides a shear wave velocity measurement. ARF impulses at different spatial locations were interleaved on a repetition time (TR) level using techniques generally known in the art. The phase difference images between each ARF image and the "off image" was then generated.

In FIG. 1, the top row shows three different Pulse Sequence Diagrams, labeled (A)-(C), respectively, used for an MR-SWE acquisition according to some of the embodiments discussed herein. The experimental setup and FUS steering locations that correspond to the Pulse Sequences (A)-(C) are shown in Images (D)-(F). The final "off image," depicted by Image (F) in this example, may be used as the displacement free reference for all ARF images.

ARF generated mechanical shear waves in an infinite viscoelastic soft solid can be modeled using the Green's Function method generally known in the art. Using the pure shear component of this model, displacement along the y-direction generated by a cylindrically symmetric forcing function along y can be calculated using the following expression:

$$u(\vec{r},t)=f(\vec{r},t) \oplus g_s(\vec{r},t) \quad (1)$$

where $\vec{r}$ is the radial position, $r=|\vec{r}|$, $f(\vec{r}, t)$ is the ARF generated force forcing function along the y direction, ⊕ denotes the convolution in both r and time t, and $$g_s(\vec{r}, t) = \frac{1}{4\pi \rho c_x} \frac{1}{\sqrt{2\pi v_s t}} \frac{r^2 - y^2}{r^3} e^{-\frac{(c_s t - r)^2}{2 v_s t}} \quad (2)$$

is the shear component of the Green's Function where is the density, $c_s$ is the shear wave speed, and $v_s$ is the kinematic shear viscosity of the media. Accrued MR phase, at time t, from these mechanical shear waves can be calculated using the following expression $$\phi(\vec{r}, t) = \gamma \int_0^t G_y(t') \cdot u(\vec{r}, t') dt' \quad (3)$$

where γ is the gyromagnetic ratio and $G_y(t)$ is the MEG waveform of the y-gradient.

Figure 2:
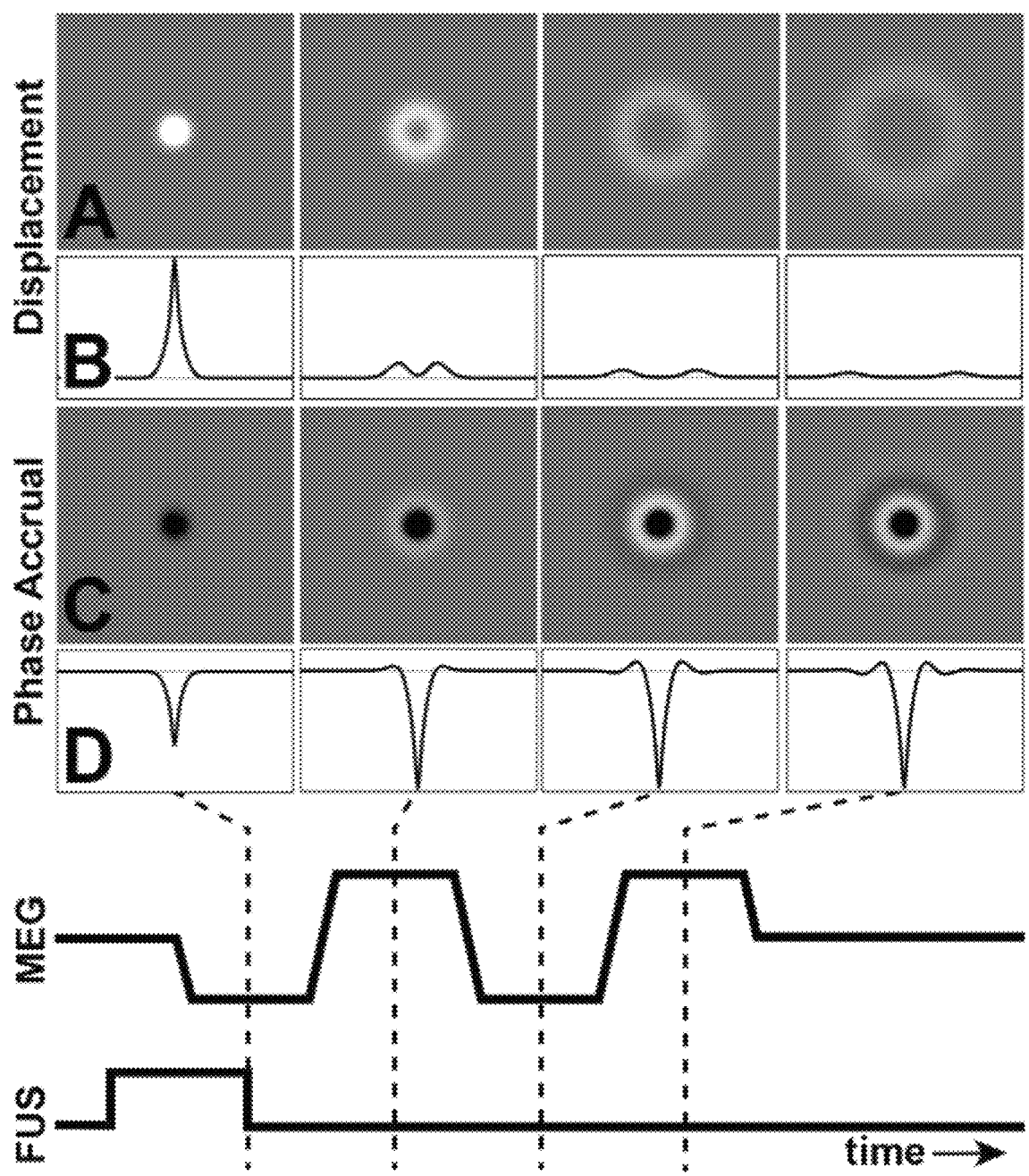
FIG. 2 shows the encoding of a transient shear wavefront in MR image phase of a coronal imaging slice at isocenter with a short MEG train oriented in the thru-slice direction.

FIG. 2 depicts a numerical simulation (using Equations 1-3) of an ARF induced shear wavefront and the accrued MR phase. More specifically, FIG. 2 shows the encoding of transient shear wavefront (Rows A, B) in MR image phase (Rows C, D) of a coronal imaging slice at isocenter with a short MEG train oriented in the thru-slice direction. Row (B) and (D) are horizontal line plots through the center of the images in Rows (A) and (C), respectively, and depict the displacement and accrued phase profiles for each simulated time-point. Each maximum or minimum ring in the image phase encodes the location of the transient shear wave at sampling times denoted by the dotted lines. The MEG and FUS waveforms denote the relative timing of the applied ARF impulse and the MR pulse sequence motion encoding gradients. While the shear wavefront is strictly positive, the wavefront position at each time-point is encoded as alternating positive and negative peaks in the phase image.

Figure 3A:
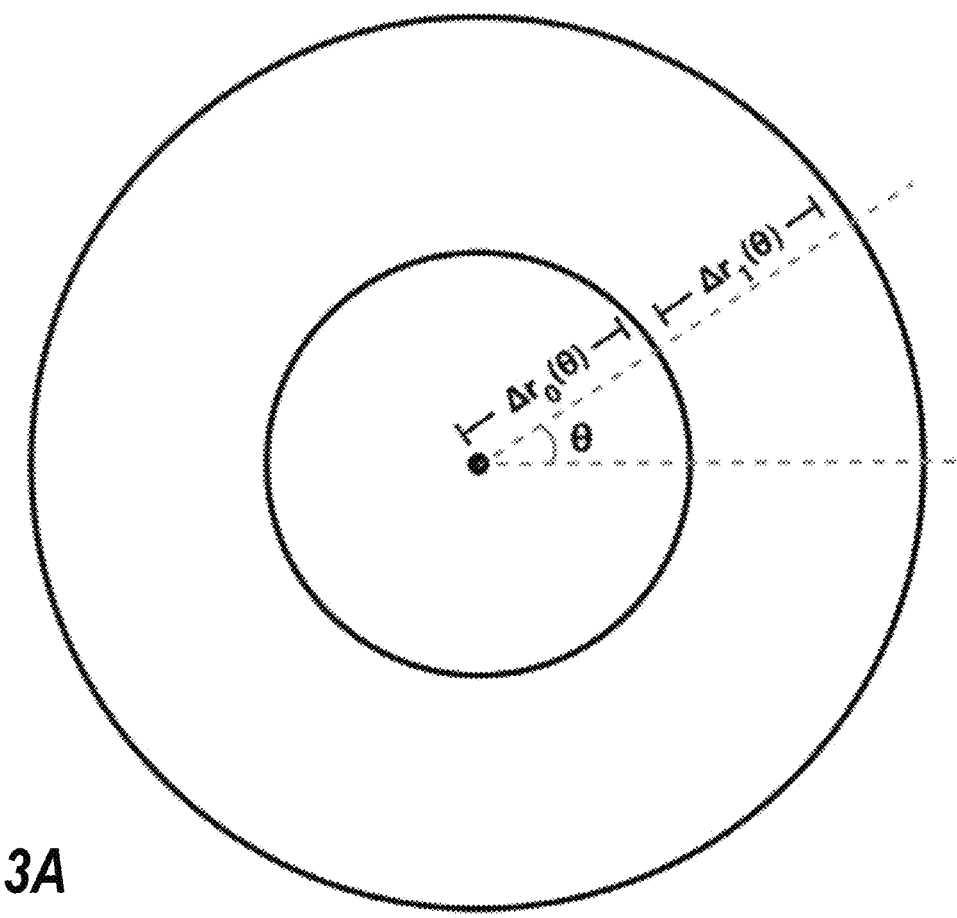
FIG. 3A shows a schematic of local extrema in the MR image phase, as may be utilized with the techniques described herein.

FIG. 3A shows a graphical depiction of the positive and negative peaks in each MR phase image. If the distance between adjacent peaks and troughs can be robustly identified, a shear wave speed estimate between the nth adjacent pair ($c_{s,n}$) can be calculated according to:

$$c_{s,n} = \begin{cases} \frac{\Delta r_0(\theta)}{\Delta t}, & n \geq 1 \\ \frac{\Delta r_n(\theta)}{t_0}, & n = 0 \end{cases} \quad (4)$$

where $\Delta r_n(e)$ is the distance between the $n^{th}$ adjacent peaktrough pair along a radius of angle, Δt is the center-to-center spacing between MEG lobes, and $t_0$ is the time between the formation of the initial shear wavefront at the ARF excitation location (origin) and the next encoded shear wavefront position.

While Δt is a parameter of the MRI pulse sequence, $t_0$ cannot be determined from the timing of the FUS and MRI pulse sequence alone and may depend on properties specific to the transducer and tissue being imaged. However, if multiple phase images are acquired so that the ARF locations are varied (as is shown in FIG. 1), $t_0$ can be numerically estimated.

Figure 3B:
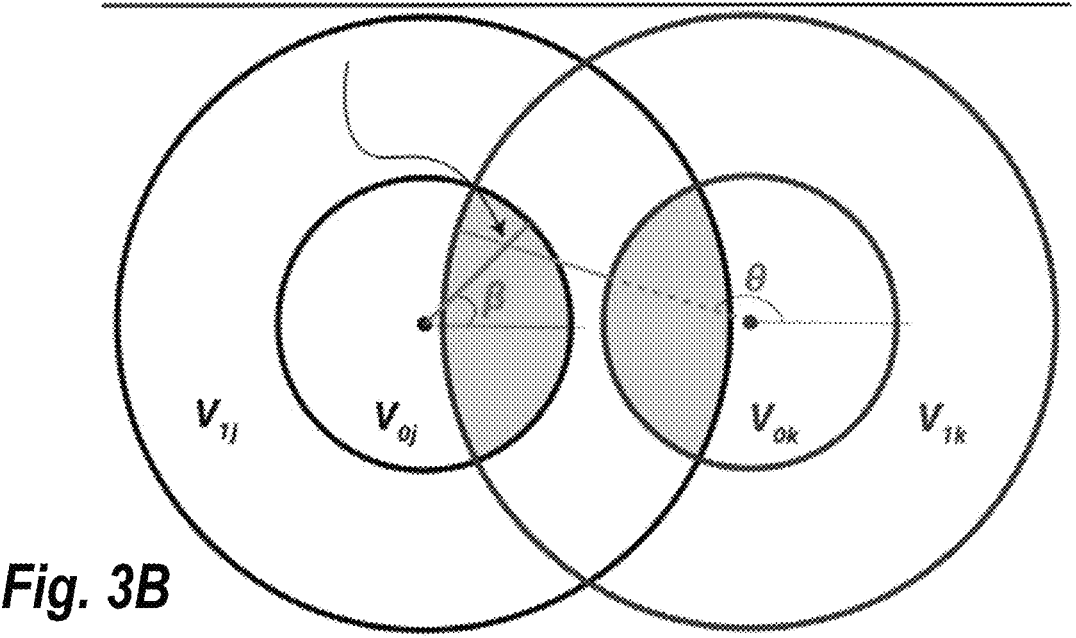
FIG. 3B shows a schematic of the local extrema from 2 phase images acquired with different ARF impulse positions, as may be utilized with the techniques described herein.

One example method of estimating $t_0$ is outlined in FIG. 3B where the subscripts j and k are used to denote parameters associated with phase images acquired with an ARF impulse located at $\vec{R_j}$ and $\overline{R_k}$, respectively. The region where $V_{0j}$ and $V_{1k}$ intersect is particularly useful. In region $V_{1k}$, the average shear wave speed along a radius of angle (radius shown as green line in FIG. 3B) can be computed using the top expression in Equation (4). In region $V_{0j}$, the distance between the first peak trough pair along a radius of angle (radius shown as magenta line in FIG. 3B) can be measured. If we assume the shear wave speed is the same along these 2 intersecting radii segments, an estimate for $t_0$ at that intersection location is obtained by dividing the first peaktrough pair distance by the measured shear wave speed. A collection of estimates of $t_0$ can be obtained by repeating this calculation for all pixels in the region where $V_{0j}$ and $V_{1k}$ intersect. The overlapping region $V_{1j}$ and $V_{0k}$ in the FIG. 3B also provides an area where $t_0$ can be estimated. In general, each multiple-point dataset will contain many of these overlapping regions. A distribution of estimates for $t_0$ (denoted by $\vec{t_0}$) can be calculated from the pixels in all overlapping regions using the following expression:

$$\vec{t}_0 = \frac{\Delta r_{0j}(\beta)}{c_{s,n}^k(\theta)}, \quad (6)$$

For all $j, k$, where $n \geq 1$ and $V_{0j} \cap V_{nk}$ where $\Delta r_{0j}(\beta)$ is the distance along a projection of angle $\beta$ between the ARF impulse location and the next wavefront position for the $j^{th}$ image and $c_{s,n}^k(\theta)$ is the calculated shear wave speed along a projection of angle $\theta$ between the $n^{th}$ peak/trough pairs of the $k^{th}$ image. It may be assumed that the time between initial formation of the shear wavefront and the first encoded shear wavefront position is the same for all ARF points in a given MR-SWE image acquisition. Thus, if multiple points are acquired in this overlapped way, the full form of Equation (4) where $t_0$=median ($\vec{t}_0$) can be used to calculate the shear wave speed.

Figure 4:
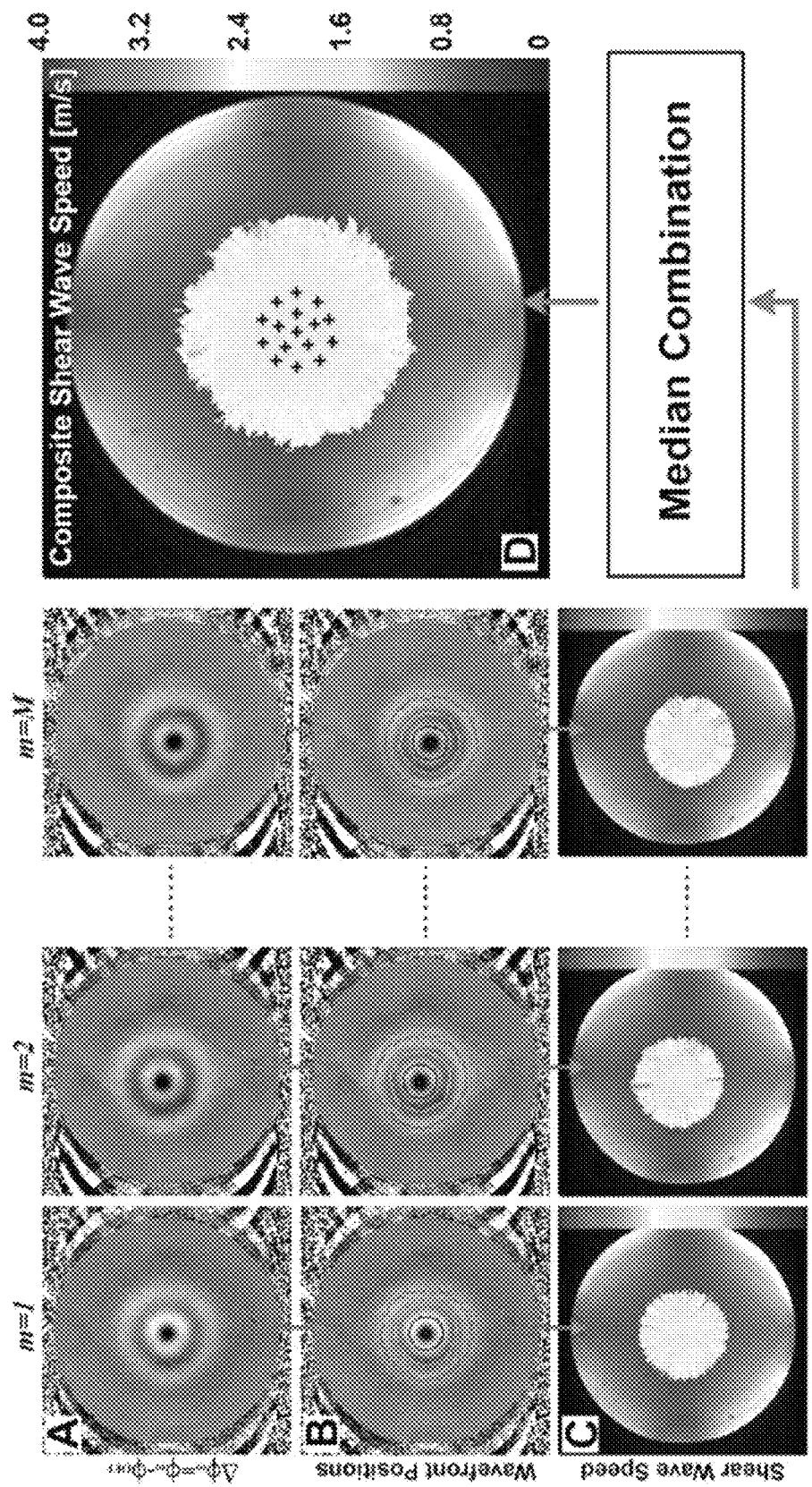
FIG. 4 illustrates the MR-SWE shear wave speed calculation and generation of a composite shear wave map, according to techniques described herein.

An example of the MR-SWE reconstruction approach and generation of a composite shear wave speed map from multiple-point data is outlined in FIG. 4. The propagating shear wavefront is visible as alternating positive and negative rings in the phase difference images (Row (A) in FIG. 4). Normalized 2D cross-correlation template matching with a 2D Gaussian shaped filter was used to extract the initial ARF impulse location for each ARF point. Using this location as the source of the cylindrically propagating wave, 1D template matching was used to generate an initial position estimate of the shear wavefront displacement peak along each radial line. To improve robustness of peak detection and allow subvoxel determination of the displacement peak position, a 1D 3rd order polynomial was fit to the local data on either side of the initial displacement peak estimate. Location of the extreme value of the fitted curve was calculated and provided the position of each shear wavefront displacement peak along each radial line (colored concentric rings in Row (B) of FIG. 4). With the wavefront positions identified for each ARF point, the shear wave speed for each phase image was calculated using the measured $t_0$ and Equation (4) (Row(C) of FIG. 4). A composite shear wave speed map was then generated as the point-wise median combination of individual shear wave maps (Image (D) in FIG. 4). This median combination comprised reporting the median value in pixels where 3 or more unique measurements of the shear wave speed existed.

As a proof of concept, MR-SWE experiments were formed in gelatin phantoms (one homogenous and one dual-stiffness) and ex-vivo bovine liver were performed using a 256-element 13-cm focal length FUS transducer (Imasonic, Besancon, France). All MR-SWE measurements were performed using a 256-element, 950 kHz frequency, FUS transducer (Imasonic, Besancon, France), with a 13 cm focal length, 2×2×8 mm full-width at half max focal spot size, and hardware and software for electronic beam steering (Image Guided Therapy, Pessac, France). The transducer was coupled to the imaging samples with a bath of deionized and degassed water (see Images (D)-(F) in FIG. 1). Custom-built single loop or 5-channel receive RF coils were used to acquire the MR signal. MR imaging was performed using a 3T scanner (MAGNETOM PrismaFIT, Siemens, Erlangen, Germany). For each MR-SWE acquisition, 16 ARF points were oriented in 2 concentric circles as shown by cross marks in Image (D) of FIG. 4. All ARF points were coplanar and contained within a radius of 8 mm about the geometric focus of the transducer. Duration of each MEG lobe was 3 ms and 4 ms for phantom and ex-vivo experiments, respectively. These durations were chosen empirically based on their ability to sufficiently encode displacements in MR image phase and to minimize spacing between encoded shear wavefront positions.

For all measurements, motion encoding was selected in the direction of the FUS beam-propagation. MR data were reconstructed offline in Matlab (R2017b, The MathWorks Inc., Natick, Mass.). Multicoil data were optimally combined to generate magnitude images and phase difference images. All MR-SWE data were zero-filled interpolated in plane to a voxel spacing of 0.5×0.5×5 mm to minimize partial-volume effects. Except for the experiment directly comparing MR-SWE to conventional MRE, all MR-SWE measurements are reported as shear wave speed maps. Conversion to shear modulus can be made using the relationship $\mu = \rho c_s^2$ described above.

The use of multilobed and single-lobed MEG encoding strategies to image ARF generated propagating wave packets was compared in a tissue-mimicking phantom. A homogeneous 125-bloom gelatin phantom (ballistics gelatin, Vyse Gelatin Co., Schiller Park, Ill.) was constructed in an acrylic cylinder (10 cm inner diameter, 15 cm height) using a recipe published previously. The phantom was doped with 2 millimolar copper (II) sulfate pentahydrate. For the single-lobed imaging protocol, 4 different images were acquired such that the delay between the start of the ARF impulse and the center of the encoding MEG lobe was 3, 6, 9, and 12 ms, respectively. This enabled the transient shear wave packet to be sampled at 4 different propagation times in 4 separate interleaved measurements.

The multilobed protocol used a 4-lobed MEG where the center-to-center spacing between adjacent lobes was 3 ms. The polarity alternated between adjacent lobes. Timing between the start of the ARF impulse and the center of each lobe was 3, 6, 9, and 12 ms, respectively. For both multilobed and single-lobed measurements the following scan and FUS parameters were used: TR/TE=47/29 ms, flip angle=23°, matrix=128×112×12, resolution=1×1×5 mm, Bandwidth=752 Hz/pixel, echo train length=7, MEG amplitude=60 mT/m, MEG slew rate=100 T/m/s, MEG lobe duration=3 ms, FUS duration=3 ms, and FUS acoustic power=106 Watts.

A second phantom experiment was performed to evaluate the relationship between gradient lobe spacing, intrinsic resolution of shear wave speed measurement, and the magnitude of phase accumulated for a given MEG duration. Two homogeneous gelatin phantoms with different mechanical properties (125-bloom and 62.5-bloom) were imaged using a 4-lobed MEG encoding strategy following an ARF excitation. MEG lobe durations of 1.2, 2, 3, 4, 5, and 6 ms were tested in each phantom. Because lobes were played back-to-back center-to-center spacing between lobes was identical to the lobe duration. For each measurement, the following scan and FUS parameters were used: TR/TE=56/38 ms, flip angle=25°, matrix=128×112×12, resolution=1×1×5 mm, bandwidth=752 Hz/Pixel, echo train length=7, MEG amplitude=60 mT/m, MEG slew rate 100 T/m/s, FUS duration=3 ms, and FUS acoustic power=71 Watts.

In tissue-mimicking phantoms, MR-SWE was evaluated and compared with conventional harmonic-excitation MRE. Two gelatin phantoms were constructed in acrylic cylinders as described above. A uniform stiffness phantom (homogeneous) was made from 125-bloom gelatin. A second phantom was constructed with 2 small balloon-filled inclusions where the gelatin inside each inclusion was 175-bloom (stiffer) and the gelatin surrounding the inclusions was 125-bloom (softer). For improved visualization of the inclusions on standard MR imaging, 125-bloom regions and 175-bloom regions were doped with 2 millimolar and 5 millimolar copper (II) sulfate pentahydrate, respectively. Before the start of experiment, phantoms were allowed to equilibrate overnight to a room temperature of approximately 22° C.

Figure 10:
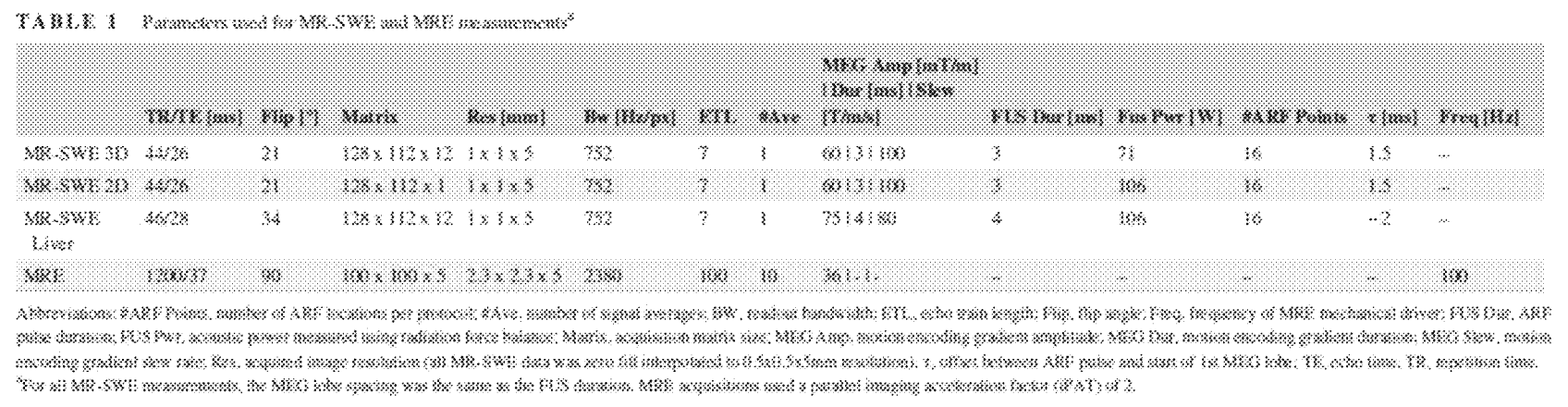

Detailed MR-SWE scan parameters for the phantom experiments are shown in FIG. 10. MR-SWE was performed using both volumetric (3D, 144 s acquisition time) and single slice (2D, 12 s acquisition time) imaging. For the volumetric imaging protocol, the shear wave speed lateral to the FUS propagation direction was measured in the 3D imaging volume. MR-SWE shear wave speed was converted to shear modulus using Equation (1). Temperature change due to ARF impulses was measured using proton resonance frequency shift (PRFS) MR thermometry. A baseline image was acquired before the start of the MR-SWE measurement. Phase subtraction of the baseline image from the MR-SWE reference image ("off" interleave) isolates the phase change due to temperature. Average field drift was measured in a region outside of the ARF deposited energy and this value was used to correct thermometry readings for field drift. For all thermometry calculations in this study, a PRFS thermal coefficient of alpha=−0.01 ppm/° C. was used.

For comparison purposes, a steady-state harmonic MIRE measurement was performed on both phantoms. A prototype 2D single-shot spin echo EPI MRE sequence was used (details in FIG. 10), and the mechanical excitation was generated by a pneumatic mechanical driver (Resoundant, Rochester, Minn.). The phantom was placed on top of the passive driver and acquisitions were in the coronal plane with MEG encoding through slice. The MIRE sequence was synchronized with the Resoundant configured to produce a harmonic steady-state 100 Hz wave excitation in the gelatin. Acquisitions were acquired over 4 phase offsets and the inversions were performed using an inline 2D multimodel direct inversion (MMDI) algorithm. A central slice was chosen for this measurement to coincide with the center location of the MR-SWE imaging slab. Standard flex and spine array coils (Siemens, Erlangen, Germany) were used during image acquisition.

A fresh (time after death less than 12 h) ex vivo bovine liver sample obtained from a local meat packing facility was placed in a 31° C. bath of normal saline. The sample and saline was placed under partial vacuum for 2 h to remove any air bubbles that may have been introduced during butchering and transport of the sample. The sample was then removed from the bath and placed in a cylindrical acrylic holder. The cylinder provides support for the MR imaging coil and one end of the holder was sealed with a thin plastic membrane to hold the sample within the cylinder (setup is shown in FIG. 1, Image (D)). Once the sample was correctly positioned, MR-SWE acquisition was performed to measure shear wave speed of the sample.

To evaluate the ability of MR-SWE to detect changes in shear wave speed due to thermal ablation, a FUS ablation was performed using the same FUS transducer used for MR-SWE. The sample was sonicated at 9 positions on a 3×3 square grid (4×4 mm) in a plane transverse to the FUS beam direction. The FUS power supplied to each point was 43.3 acoustic watts for a duration of 21.5 s per point with a 5.38 s pause between each point. This ablation pattern was repeated twice at the exact same sonication locations. During thermal ablation, a segmented EPI MR thermometry protocol (without MEGs) with the following scan parameters was used: repetition time (TR)/echo time (TE)=28/22 ms, flip angle=27°, matrix=128×112×12, resolution=1×1×2 mm, bandwidth=752 Hz/pixel, echo train length=7. Temperature maps for the ablation were reconstructed using the PRFS method. Using the temperature maps, thermal dose in cumulative equivalent minutes at 43° C. (CEM43) was calculated using previously described methods. By the time the sample was positioned, and imaging was localized, it was likely that the sample cooled significantly from the initial 31° C. water bath temperature. Exact sample temperature at time of ablation was not known. Room temperature (22° C.) was used as the starting temperature for thermal dose calculations. The MR-SWE measurement was repeated after the thermal ablation and compared with pre-ablation MR-SWE measurements. All MR-SWE acquisition parameters used for the measurements are shown in FIG. 10.

Figure 5:
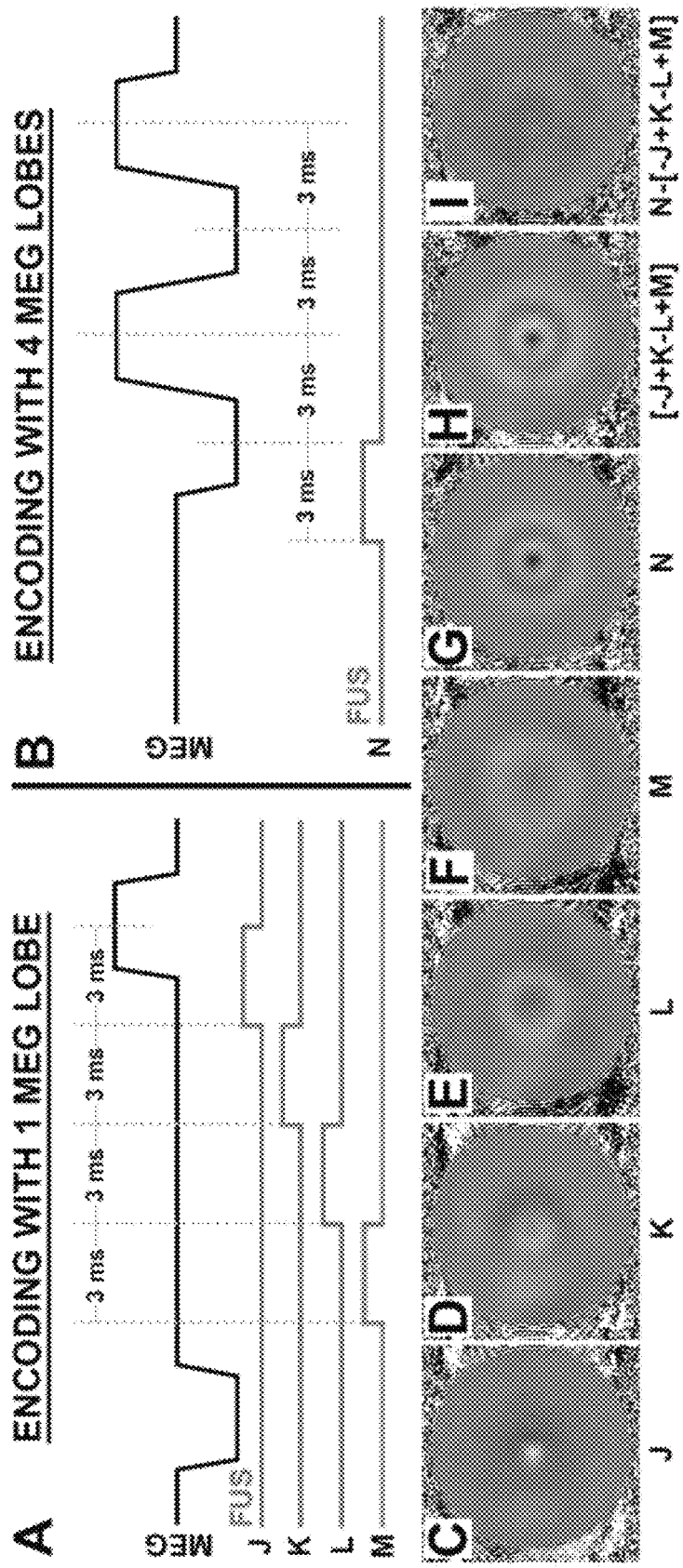
FIG. 5 provides a comparison of a single lobe and 4-lobe MEG encoding strategies, as may be implemented with the techniques described herein.

FIG. 5 shows a comparison of single lobe (labelled (A)) and 4-lobe (labelled (B)) MEG encoding strategies. In this example, letters J, K, L, and M are used to represent acquisition from single-lobed encoding where delay between start of 3 ms FUS pulse and center of the MEG lobe is 3, 6, 9, 12 ms, respectively. Letter N is used to represent 4-lobed acquisition where delay between start of 3 ms FUS pulse and center of first MEG lobe is 3 ms. Phase images for the single lobe acquisition minus a reference phase image (no FUS) are depicted in (Images (C)-(F)). Phase image using the 4-lobed acquisition minus a reference phase image (no FUS) is depicted in Image (G). Multiple concentric rings of alternating polarity surrounding a central encoded location are visible. Image (H) shows a composite of Images (C)-(F) determined by summing all images and alternating sign of adjacent pairs. This combination effectively shows that the 4-lobed acquisition contains information encoded in the separate 4 single lobe measurements. The difference between Image (G) and Image (H) is shown in Image (I). These results indicate that the 4-lobed encoding scheme samples the same propagation times that were imaged in single-lobed measurements.

Results from the second phantom study (shown in FIG. 6) demonstrate that longer MEG lobe durations (using a 4-lobed MEG encoding scheme) result in increased phase accrual and coarser shear wave speed map resolution. For the MR-SWE algorithm, the shear wave speed of the media multiplied by the MEG spacing provides a metric for evaluating the intrinsic resolution of the multilobed encoding scheme. In the 125-bloom phantom (Row (A)), 6, 5, 4, 3, and 2 ms MEG lobe durations resulted in intrinsic resolutions of 14.6, 12.0, 9.2, 6.8, and 4.8 mm, respectively. For the 1.2 ms MEG lobe duration, encoded shear wavefronts could not be resolved. In the 62.5-bloom phantom (Row (B)), 6, 5, 4, and 3 ms MEG durations resulted in intrinsic resolutions of 6.7, 5.5, 4.7, 3.3 mm, respectively. For the 2 and 1.2 ms MEG lobe durations, encoded share wavefronts could not be easily resolved.

Figure 6:
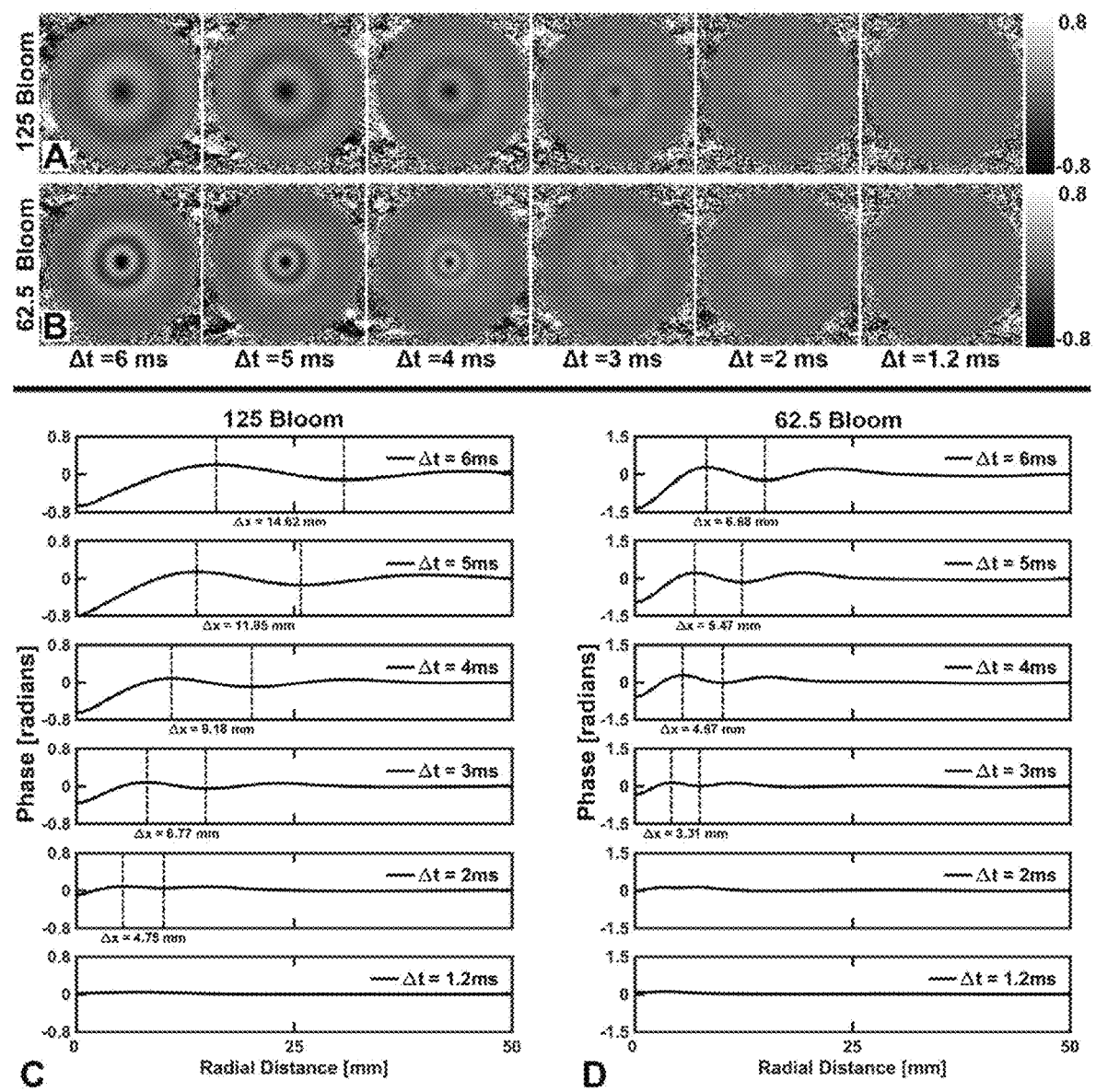
FIG. 6 shows examples of phase difference images of 125-bloom and 62.5-bloom phantoms.

Continuing with reference to FIG. 6, all radial rays were averaged to generate the line plots shown in Plots (C) for the 125-bloom phantom and Plots (D) for the 62.5 bloom phantom. The vertical dotted lines in each figure denote the first local maximum and second local minimum in each line plot. The distance between these dotted lines provides a measure of the spacing between sampled shear wavefronts. For decreasing Δt, the spacing between encoded wavefronts decreases (finer resolution of sampled shear wavefront positions). Decreasing this distance results in finer resolution shear wave speed maps. However, the magnitude of the phase accrual also decreases with decreasing Δt, making it more difficult to detect the encoded wave front positions.

Figure 7:
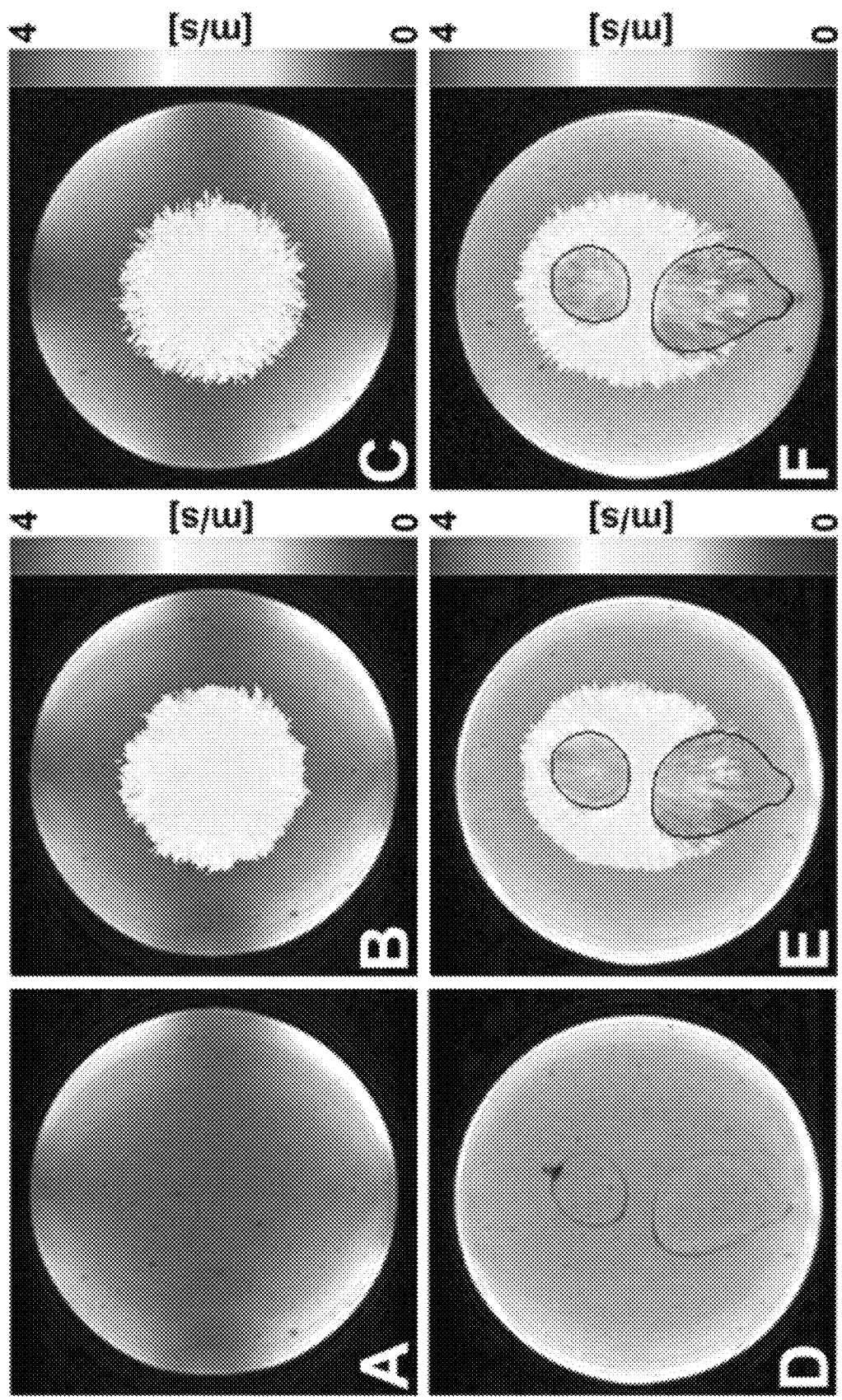
FIG. 7 shows examples of MR-SWE shear wave speed measurements in homogeneous and inclusion phantom, as well as corresponding magnitude images.

FIG. 7 shows example MR-SWE shear wave speed measurements in homogeneous (Images (A)-(C)) and inclusion (Images (D)-(F)) phantom. The second and third column, respectively, depict the calculated shear wave speed for 3D and 2D MR-SWE acquisitions. Both 3D and 2D acquisitions produced comparable composite shear wave speed maps, albeit for 2D measurement, higher power ARF impulses (106 acoustic watts instead of 71 acoustic watts) were used and phase images used to calculate the shear wave speed were noisier due to the shorter acquisition time.

In Image (D) of FIG. 7, the border of the 2 inclusions can be seen by the decrease in signal intensity. Inclusion borders were traced and overlaid as black lines on the MR-SWE maps in Images (E) and (F) shown in FIG. 7. The regions of increased shear wave speed are well encapsulated by the traced inclusion boundary. In the homogeneous phantom, the shear wave speed mean and SD (μ±σ) measured over a centrally located region of interest (ROI) was 2.06±0.04 and 2.07±0.06 m/s for the 3D and 2D acquisitions, respectively. In the inclusion phantom, the mean shear wave speeds of the inclusions were 2.84±0.11 and 2.84±0.15 m/s for 3D and 2D acquisitions, respectively. Mean shear wave speed of gelatin surrounding the inclusions was 2.16±0.06 and 2.13±0.09 m/s for 3D and 2D acquisitions, respectively, in close agreement with what was measured in the homogenous phantom.

Figure 8:
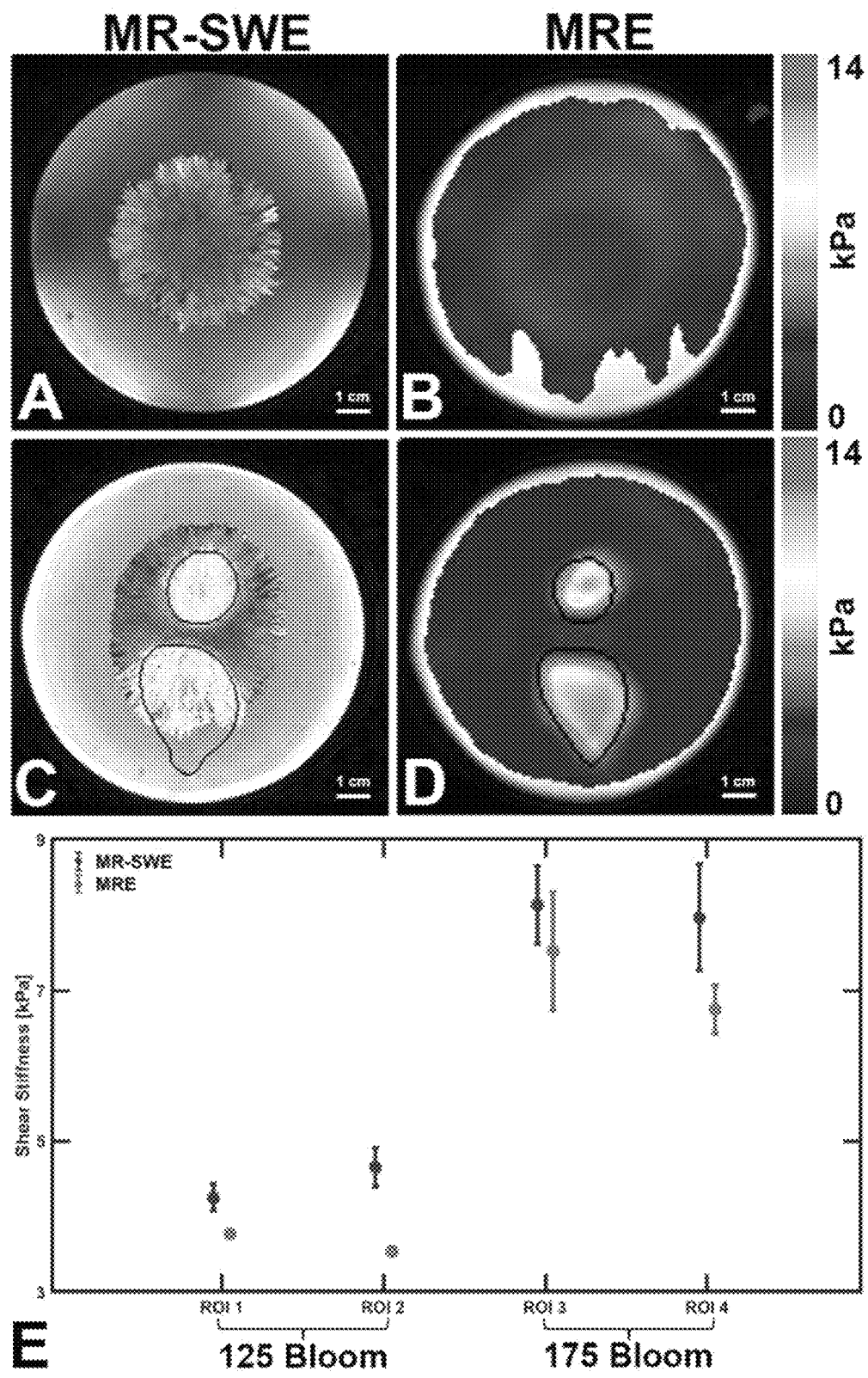
FIG. 8 provides a comparison of examples MR-SWE and MRE shear modulus maps in homogeneous and inclusion phantoms.

FIG. 8 shows a comparison of MR-SWE (Images (A),(C)) and MRE (Images (B),(D)) shear modulus maps in homogeneous (Images (A),(B)) and inclusion (Images (C),(D)) phantoms. Black overlays in Images (C) and (D) denote the inclusion borders. White scale bars correspond to 1 cm. Mean and SD of MR-SWE and MRE measurements in homogeneous (ROI 1) and inclusion (ROI 2-4) phantoms shown in Image (E) with ROIs (1 and 2) corresponding to 125 Bloom regions and ROIs (3 and 4) corresponding to 175 Bloom regions. In all ROIs, a 2-sample t-test showed that MR-SWE and MRE measured values were statistically different (P<0.01)

In the homogeneous phantom shown in FIG. 8, mean shear stiffness was 4.25±0.18 and 3.77±0.03 kPa for MR-SWE and MRE measurements, respectively. In the inclusion phantom, average shear stiffness in the softer surrounding region was 4.65±0.25 and 3.54±0.04 kPa for MR-SWE and MRE measurements. The top inclusion had an average shear stiffness of 8.13±0.51 and 7.52±0.78 kPa for MR-SWE and MRE measurements, respectively. The bottom inclusion had an average shear stiffness of 7.99±0.70 and 6.75±0.32 kPa for MR-SWE and MRE measurements. Plot (E) in FIG. 8 graphically depicts the mean and SD of the shear stiffness measurement in the homogeneous region and within the inclusions.

Figure 9:
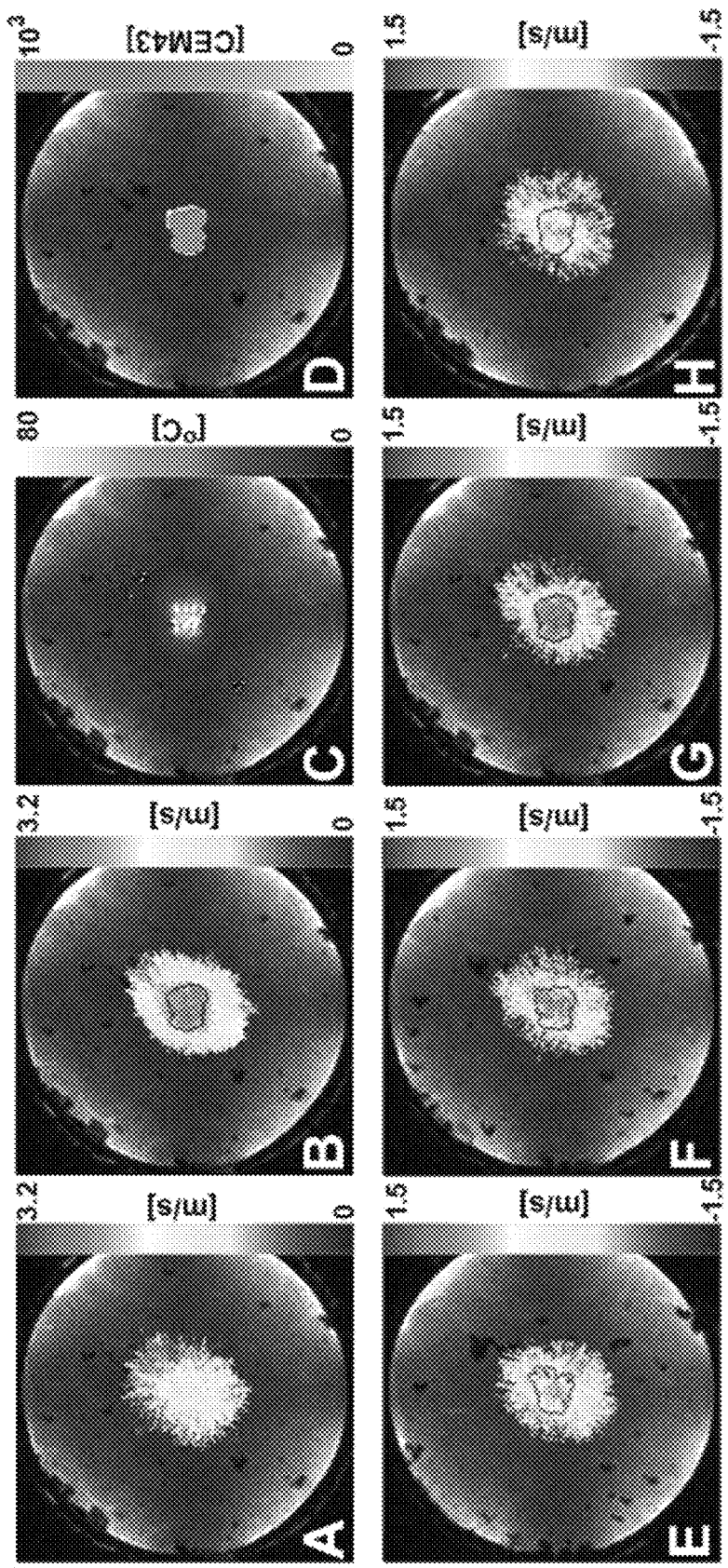
FIG. 9 shows an example of MR-SWE shear wave speed maps for the ex vivo ablation experiment described herein.

FIG. 9 presents results from the ex vivo bovine liver experiment. Images (A) and (B), respectively, depict the MR-SWE shear wave speed measurement before and after tissue ablation. The post ablation MR-SWE measurement shows increased shear wave speeds in the ablated region. Image (C) shows the maximum intensity projection (MIP) of MR thermometry readings acquired during the ablation. Measured peak temperature change exceeded 80° C. Image (D) in FIG. 9 shows the total calculated thermal dose distribution. The 240 CEM43 isodose line circumscribing the ablated region was determined and displayed as a black overlay on the shear wave speed map shown in Image (B). All points circumscribed by the isodose line received a dose of at least 240 CEM43. Within the thermal dose boundary in Image (B) (n=581 pixels), the mean shear wave speed before and after ablation was 1.65±0.18 and 2.52±0.18 m/s, respectively. A 2-sample t-test showed that this shear wave speed change was statistically significant, P-value<0.001. Images (E)-(H) depicts the difference in measured shear wave speed (post ablation minus pre ablation) for 4 adjacent imaging slices. In each of the slices, the measured change in shear wave speed within the 240 CEM43 dose region was 0.42, 0.64, 0.87, and 0.32 m/s for Images (E)-(H), respectively. For the MR-SWE acquisition, the ARF impulses were coplanar and located between slices shown in Image (F) and Image (G). Slices nearest the plane of the ARF impulses and ablation sonication showed the largest change in measured shear wave speed.

Figure 11:
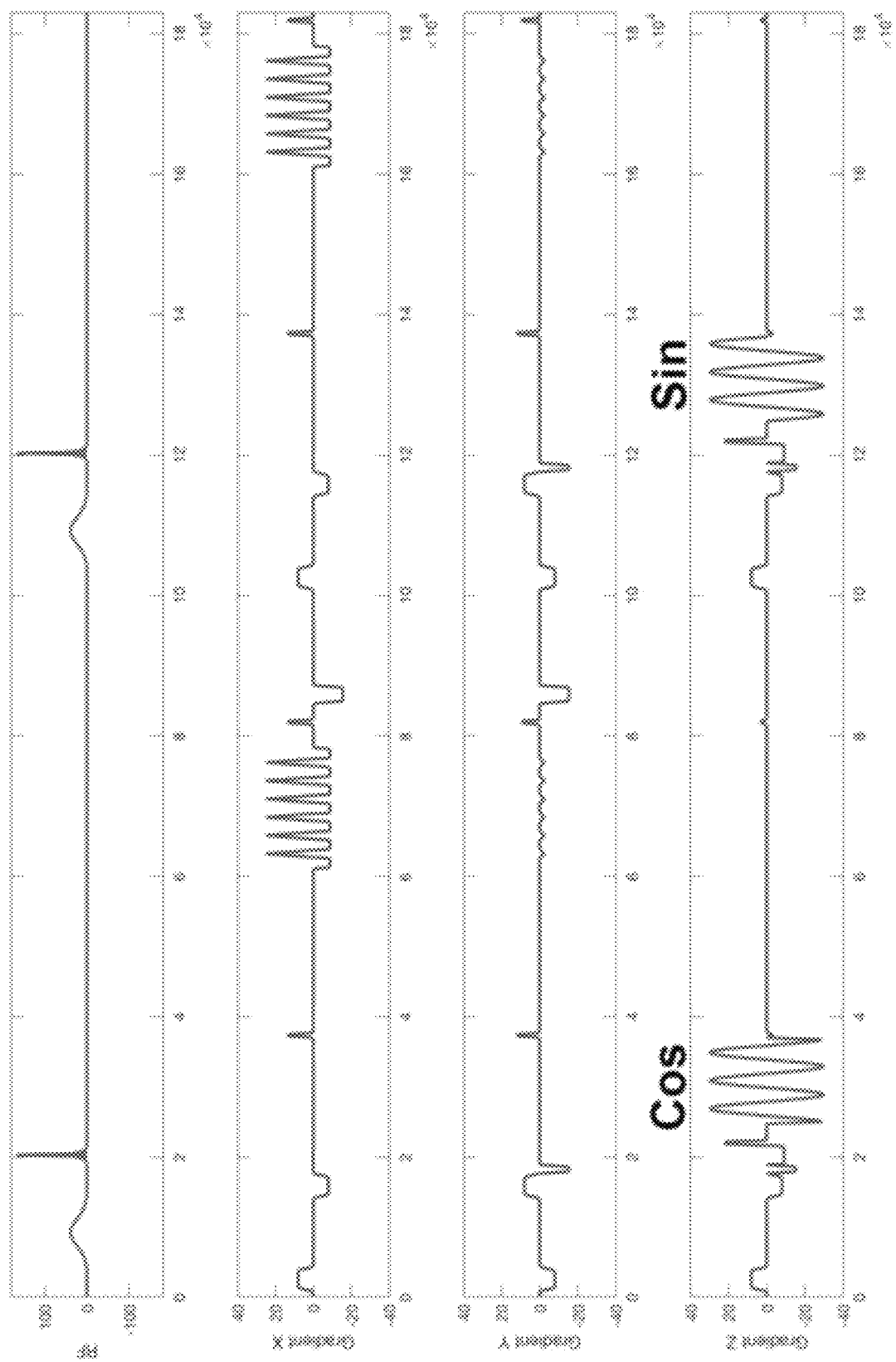
FIG. 11 shows a pulse sequence diagram for performing mapping shear wave velocity, according to the techniques described herein.

The MR-SWE technique described above includes a wavespeed calculation method that can be difficult to implement in some settings. Additionally that implementation of MR-SWE may be less robust in the presence of noise as it relies on locating discrete maxima in the encoded shear wave propagation wavefront. This could result in low resolution estimates of stiffness in the region of interest. To address these issues, in some embodiments, an alternate encoding and post-processing method referred to herein as MR-SWE2 can be employed. The trapezoidal motion encoding gradient waveforms are replaced with sinusoidal shaped motion encoding gradients. The MRI pulse sequence is depicted in FIG. 11. A segmented EPI pulse sequence is executed where Sin and Cos shaped motion-encoding gradients are interleaved on a repetition time (TR) level. This interleaving strategy is performed until k-space is sufficiently acquired to reconstruct a volume. An "FUS off" image is also acquired as a reference.

In MR-SWE2, the MRI pulse sequence is precisely timed with the ARF generated impulses. Let us denote the phase of the image acquired using the cosine MEG and phase of the image acquired using the sine MEG to be $\phi_{cos}$ and $\phi_{sin}$, respectively. Let us denote the phase of a reference image (FUS off) image by $\phi_0$. This "FUS off" image is used to remove any background phase from $\phi_{cos}$ and $\phi_{sin}$. Using the off images, the following quantities are computed:

$$\Delta\phi_{cos} = \phi_{cos} - \phi_0 \qquad (7)$$

$$\Delta\phi_{sin} = \phi_{sin} - \phi_0 \qquad (8)$$

The two phase difference images in Equations (7) and (8) are then combined as follows to generate a complex image (Z):

$$Z = \Delta\phi_{cos} + i\Delta\phi_{sin} \qquad (9)$$

where $i=\sqrt{-1}$. If the location of the initial ARF impulse is known or is measured it can be used to define a central axis about which a cylindrical coordinate system can be established. The shear wave speed can then be calculated according to:

$$c_s = \frac{\omega}{\dfrac{d}{dr}(\angle Z)} \qquad (10)$$

where ω is the angular frequency of the sine and cosine MEG waveforms, $\angle Z$ denotes the phase of the complex image Z. The derivative is taken with respect to the radial position in the cylindrical coordinate system. Again the origin of this coordinate system, $(x_0, y_0)$, is the location of the initial ARF impulse. This derivative may be taken by computing the phase difference between adjacent pixels, which obviates the need for any phase unwrapping.

There are two possible ways of computing the denominator of the expression in Equation (10). The first method is performed stepwise with conversion to and from polar coordinates. First, $\angle Z$ is converted to polar coordinates (r, θ), where the origin of the polar coordinates is at the impulse location $(x_0, y_0)$. Next, the derivative is computed with respect to r. Then, the result is transformed back to (x,y) Cartesian space.

The second method of computing the denominator does not require a coordinate transform. For notation purposes, let us define $f(x, y)=\angle Z$. From the chain rule, we can write the following:

$$\frac{df(x, y)}{dr} = \frac{\partial f(x, y)}{\partial x}\frac{dx}{dr} + \frac{\partial f(x, y)}{\partial y}\frac{dy}{dr} \quad (11)$$

In polar coordinates, we have $$\frac{dx}{dr} = \cos\theta, \frac{dy}{dr} = \sin\theta \quad (12)$$

and we can denote the partial derivatives as gradients along the x and y dimension of the image. Thus Equation (11) becomes $$\frac{df(x, y)}{dr} = \nabla_x(f(x, y)) \cdot \cos(\theta(x, y)) + \nabla_y(f(x, y)) \cdot \sin(\theta(x, y)) \quad (13)$$

where the dependence of angle θ on position x and y is written explicitly. Gradients in Equation (13) can be calculated in Cartesian space and phase unwrapping can be performed simultaneously. These gradients can be computed as follows:

$$\nabla_x(f(x_n, y_n)) = \quad (14)$$
$$[L(f(x_{n+1}, y_n) \cdot f^*(x_n, y_n)) + L(f(x_n, y_n) \cdot f^*(x_{n-1}, y_n))] \cdot \frac{1}{2\delta_x}$$

$$\nabla_y(f(x_n, y_n)) = \quad (15)$$
$$[L(f(x_n, y_{n+1}) \cdot f^*(x_n, y_n)) + L(f(x_n, y_n) \cdot f^*(x_n, y_{n-1}))] \cdot \frac{1}{2\delta_y}$$

where δx is the pixel spacing in x and δy is the pixel spacing in y. The angle θ as a function of pixel position (x,y) can also be computed using the following relation:

$$\theta(x_n, y_n) = \tan^{-1}\left(\frac{\delta_y \cdot (y_n - y_0)}{\delta_x \cdot (x_n - x_0)}\right) \quad (16)$$

Thus using the result from Equations (13)-(16) the denominator in Equation (15) can be calculated directly without first converting image to polar coordinates.

The MR-SWE2 method uses Equation (15) to calculate shear wave speed maps for a single ARF excitation location. However like in the original MR-SWE method discussed above, it is also possible to perform multiple acquisitions in an interleaved fashion such that the location of the FUS induces ARF excitation is different for each imaging acquisition. Each measurement can then be combined in a noise optimal fashion to produce a composite shear wave speed map that has higher signal to noise and provide measurements over a larger region of interest.

Figure 12:
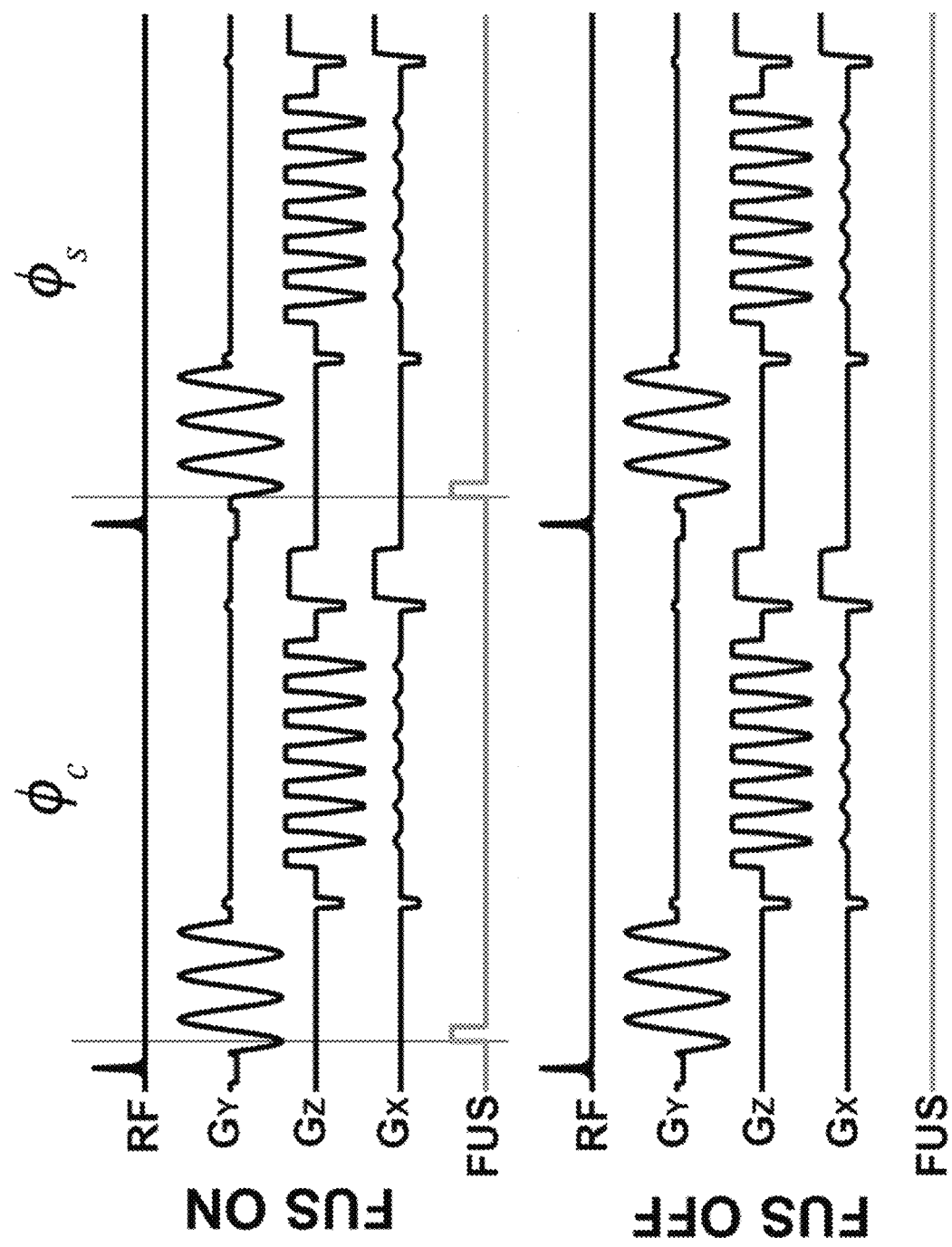
FIG. 12 shows a pulse sequence diagram for performing mapping shear wave velocity, according to the techniques described herein.

An alternative pulse sequence for encoding the Sin and Cos phase images is shown in FIG. 12. The motion-encoding gradient shape is the same sinusoid shape for both interleaved acquisitions. To achieve the Sin and Cos encodings, the timing of the ARF excitation relative to the motion-encoding gradient is shifted by one quarter of a cycle. This enables the Cos and Sin phase images ($\phi_{cos}$ and $\phi_{sin}$) to be acquired by shifting the relative timing of the ultrasound pulse and the motion-encoding gradient.

Figure 13:
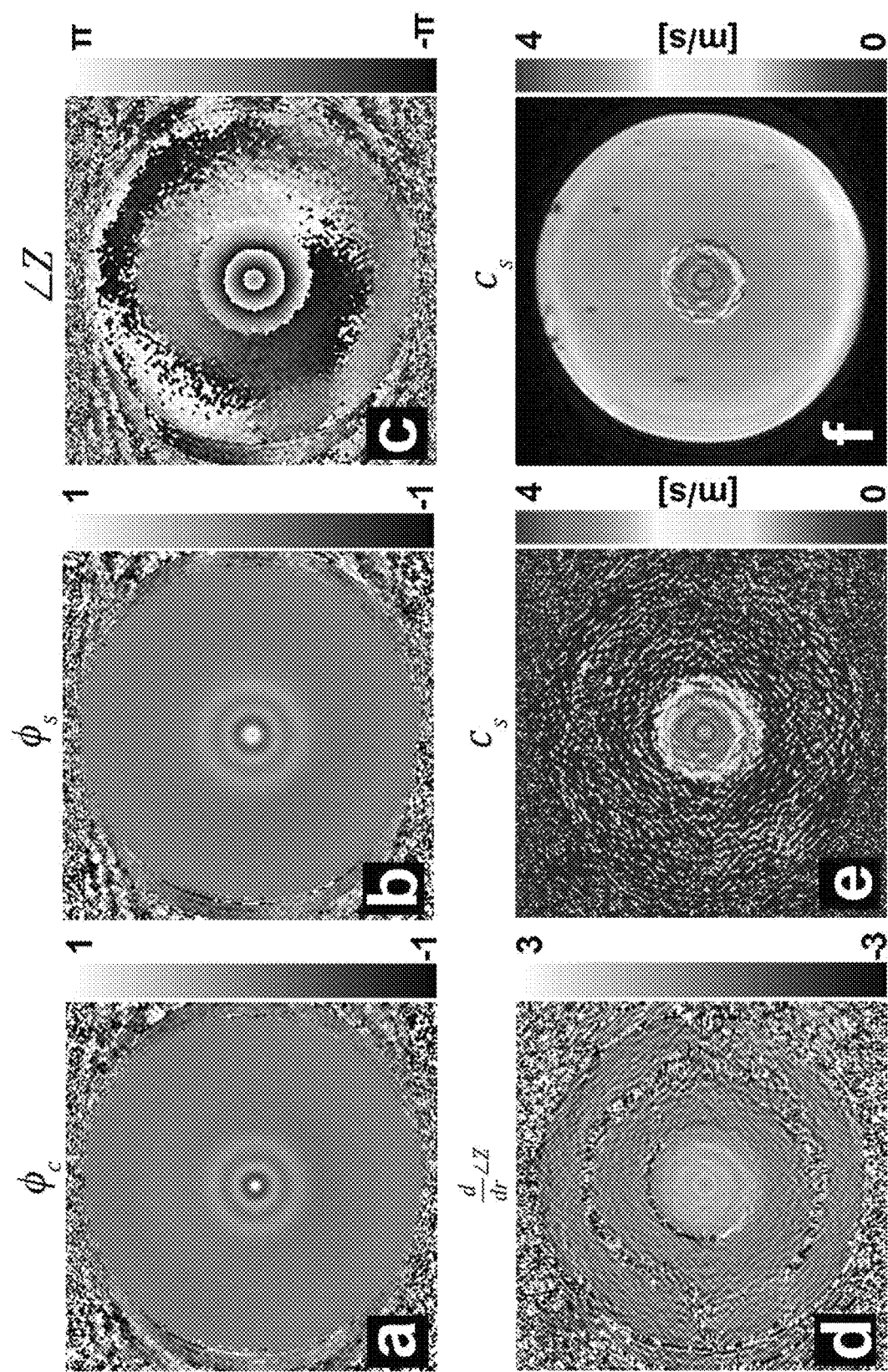
FIG. 13 illustrates the MR-SWE2 shear wave speed calculation and generation of shear wave map for a single ARF location, according to techniques described herein.

FIG. 13 shows an example of the MR-SWE2 calculation for phase images collected at a single point. Images (a) and (b) show the Cos and Sin phase images, respectively. Image (c) shows the phase of the complex image (Z). The radial derivative of ∠Z is depicted in Image (d). The calculated shear wave speed using Equation 10 is shown in Image (e). The masked shear wave speed map from Image (e) overlaid on the MRI magnitude image is shown in Image (f). MR-SWE2 may provide several improvements over the MR-SWE method discussed earlier in this disclosure. For example, MR-SWE2 offers a more automated and robust processing algorithm, and the possibility of generating higher resolution shear wave speed maps for a given acquisition time. MR-SWE2 calculates shear wave speed continuously in space whereas the MR-SWE was restricted to discrete points that were fixed distances from the ARF excitation.

Figure 14:
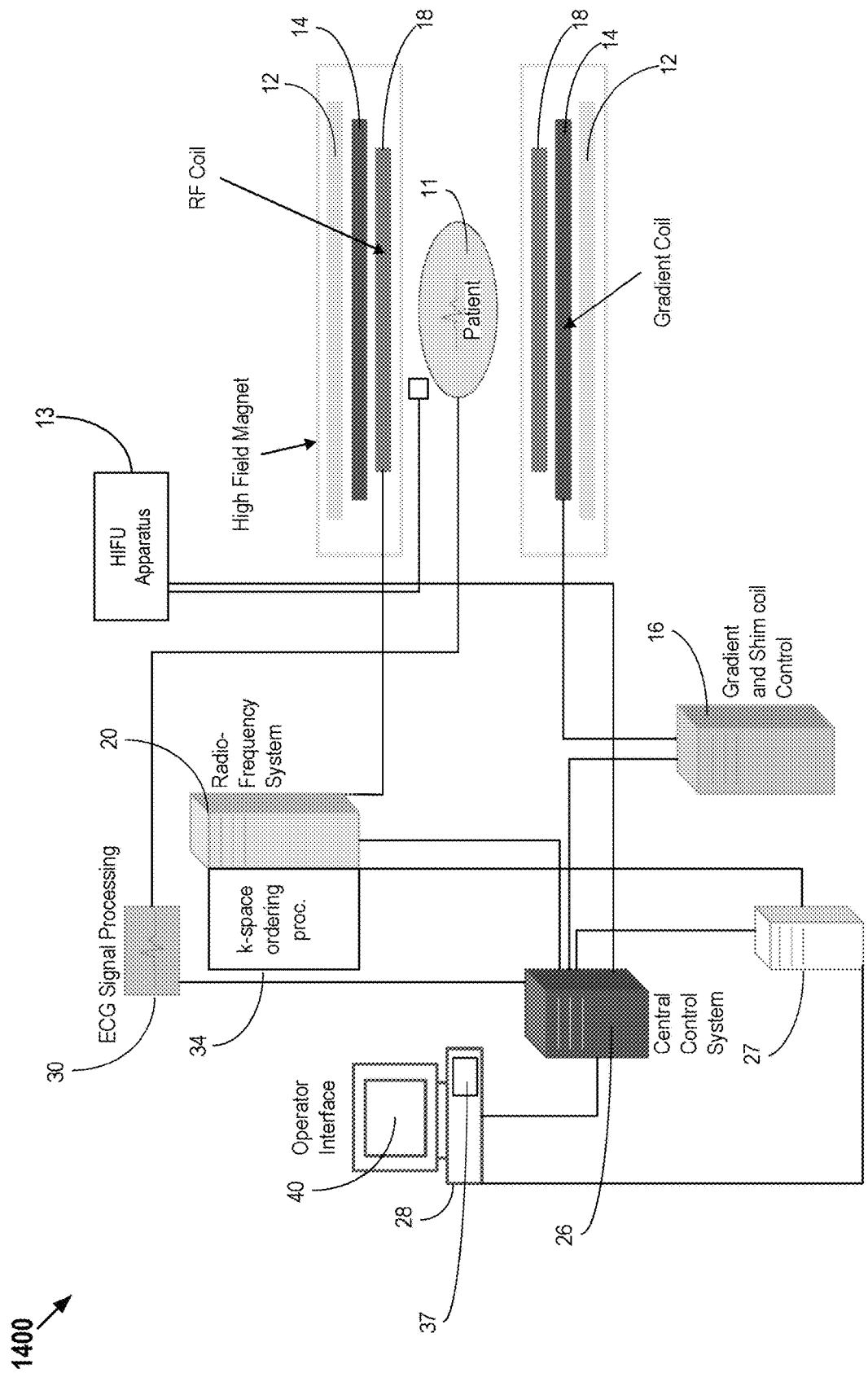
FIG. 14 shows an example system for mapping shear wave velocity and shear modulus in biological tissues, according to some embodiments.

FIG. 14 shows an example system 1400 for mapping shear wave velocity and shear modulus in biological tissues, according to some embodiments. In system 1400, magnetic coils 12 create a static base magnetic field in the body of patient 11 to be imaged and positioned on a table. Within the magnet system are gradient coils 14 for producing position dependent magnetic field gradients superimposed on the static magnetic field. Gradient coils 14, in response to gradient signals supplied thereto by a gradient and shim coil control module 16, produce position dependent and shimmed magnetic field gradients in three orthogonal directions and generates magnetic field pulse sequences. The shimmed gradients compensate for inhomogeneity and variability in an MR imaging device magnetic field resulting from patient anatomical variation and other sources. The magnetic field gradients include a slice-selection gradient magnetic field, a phase-encoding gradient magnetic field and a readout gradient magnetic field that are applied to patient 11.

Further RF (radio frequency) module 20 provides RF pulse signals to RF coil 18, which in response produces magnetic field pulses which rotate the spins of the protons in the imaged body of the patient 11 by ninety degrees or by one hundred and eighty degrees for so-called "spin echo" imaging, or by angles less than or equal to 90 degrees for so-called "gradient echo" imaging. Gradient and shim coil control module 16 in conjunction with RF module 20, as directed by central control computer 26, control slice-selection, phase-encoding, readout gradient magnetic fields, radio frequency transmission, and magnetic resonance signal detection, to acquire magnetic resonance signals representing planar slices of patient 11.

In response to applied RF pulse signals, the RF coil 18 receives MR signals, i.e., signals from the excited protons within the body as they return to an equilibrium position established by the static and gradient magnetic fields. The MR signals are detected and processed by a detector within RF module 20 and k-space component processor unit 34 to provide an MR dataset to an image data processor for processing into an image. In some embodiments, the image data processor is located in central control computer 26. However, in other embodiments such as the one depicted in FIG. 14, the image data processor is located in a separate unit 27. Electrocardiogram (ECG) synchronization signal generator 30 provides ECG signals used for pulse sequence and imaging synchronization. A two or three dimensional k-space storage array of individual data elements in k-space component processor unit 34 stores corresponding individual frequency components which comprises an MR dataset. The k-space array of individual data elements has a designated center and individual data elements individually have a radius to the designated center.

A magnetic field generator (comprising coils 12, 14 and 18) generates a magnetic field for use in acquiring multiple individual frequency components corresponding to individual data elements in the storage array. The individual frequency components are successively acquired in an order in which radius of respective corresponding individual data elements increases and decreases along a substantially spiral path as the multiple individual frequency components is sequentially acquired during acquisition of an MR dataset representing an MR image. A storage processor in the k-space component processor unit 34 stores individual frequency components acquired using the magnetic field in corresponding individual data elements in the array. The radius of respective corresponding individual data elements alternately increases and decreases as multiple sequential individual frequency components are acquired. The magnetic field acquires individual frequency components in an order corresponding to a sequence of substantially adjacent individual data elements in the array and magnetic field gradient change between successively acquired frequency components is substantially minimized.

Central control computer 26 uses information stored in an internal database to process the detected MR signals in a coordinated manner to generate high quality images of a selected slice(s) of the body (e.g., using the image data processor) and adjusts other parameters of system 1400. The stored information comprises predetermined pulse sequence and magnetic field gradient and strength data as well as data indicating timing, orientation and spatial volume of gradient magnetic fields to be applied in imaging. Generated images are presented on display 40 of the operator interface. Computer 28 of the operator interface includes a graphical user interface (GUI) enabling user interaction with central control computer 26 and enables user modification of magnetic resonance imaging signals in substantially real time. Display processor 37 processes the magnetic resonance signals to provide image representative data for display on display 40, for example.

FIG. 14 also shows a high intensity focused ultrasound (HIFU) apparatus 13 that, in this example, is operated (activated) by a signal from central control computer 26. The HIFU apparatus 13 comprises a multi-element transducer for converting between acoustic and electrical energies. The HIFU apparatus 13 may also include a transmit beamformer that relatively delays and apodizes signals for different elements of the aforementioned transducer. The transducer may thus be used to generate a beam that induces a mechanical wave within the patient 11 for MR imaging of strain or elasticity according to the techniques described herein. All or a portion of the HIFU apparatus 13 may be positioned in the bore of the MRI system described above.

The embodiments of the present disclosure may be implemented with any combination of hardware and software. In addition, the embodiments of the present disclosure may be included in an article of manufacture (e.g., one or more computer program products) having, for example, computer-readable, non-transitory media. The media has embodied therein, for instance, computer readable program code for providing and facilitating the mechanisms of the embodiments of the present disclosure. The article of manufacture can be included as part of a computer system or sold separately.

The term "computer readable medium" as used herein refers to any medium that participates in providing instructions to the processor for execution. A computer readable medium may take many forms including, but not limited to, non-volatile media, volatile media, and transmission media. Non-limiting examples of non-volatile media include optical disks, solid state drives, magnetic disks, and magneto-optical disks, such as hard disk or removable media drive. One non-limiting example of volatile media is dynamic memory. Non-limiting examples of transmission media include coaxial cables, copper wire, and fiber optics, including the wires that make up one or more buses. Transmission media may also take the form of acoustic or light waves, such as those generated during radio wave and infrared data communications.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

The functions and process steps herein may be performed automatically or wholly or partially in response to user command. An activity (including a step) performed automatically is performed in response to one or more executable instructions or device operation without user direct initiation of the activity.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. 112(f), unless the element is expressly recited using the phrase "means for."

The invention claimed is:

1. A method for mapping shear wave velocity in biological tissues, the method comprising:
   using an ultrasound transducer to generate mechanical excitations at a plurality of locations in a region of interest, wherein using the ultrasound transducer to generate mechanical excitations comprises:
using the ultrasound transducer to generate a first mechanical excitation at a first origin location and a second mechanical excitation at a second origin location;
using an MRI system to capture a phase image of each mechanical excitation, wherein multi-lobed motion encoding gradients (MEGs) of the MRI system encode a propagating shear wavefront caused by the mechanical excitation wherein the propagating shear wavefront is encoded at multiple propagation distances in the phase image, wherein the MEGs are trapezoidal shaped waveforms, wherein using the MRI system to capture the phase image of each mechanical excitation comprises:
using the MRI system to capture a first phase image of the first mechanical excitation, wherein the multi-lobed MEGs of the MRI system encode a first propagating shear wavefront caused by the first mechanical excitation wherein the first propagating shear wavefront is encoded at multiple propagation distances in the first phase image, and
using the MRI system to capture a second phase image of the second mechanical excitation, wherein the multi-lobed MEGs of the MRI system encode a second propagating shear wavefront caused by the second mechanical excitation wherein the second propagating shear wavefront is encoded at multiple propagation distances in the second phase image;
generating a plurality of shear wave velocity maps based on the phase images, wherein each shear wave velocity map depicts velocity between adjacent propagating shear wavefronts;
combining a plurality of shear wave speed values to generate a composite shear wave velocity map of the region of interest;
identifying an overlapping area between a first encoded wavefront in the first phase image and a second encoded wavefront in the second phase image;
calculating a shear wave speed in the overlapping area;
measuring a distance between the first origin location and the first encoded wavefront;
calculating a propagation time using the measured distance, wherein the propagation time is a time between the first mechanical excitation and the first encoded wavefront; and
calculating a shear wave speed in the area between the first origin location and the first encoded wavefront using the propagation time and the measured distance.

2. The method of claim 1, wherein the velocity between adjacent propagating shear wavefronts is calculated by dividing a radial distance separating the adjacent propagating shear wavefronts by spacing of the MEGs during capture of the phase images.

3. The method of claim 1, wherein the MRI system interleaves acquisition of the phase images on a repetition time level.

4. The method of claim 3, further comprising:
acquire a reference image of a region of interest without any excitation from the ultrasound transducer in the region of interest;
prior to generation of the shear wave velocity maps, subtracting the reference MRI image from each phase image to minimize phase variations not caused by the mechanical excitations.

5. The method of claim 1, wherein the ultrasound transducer generates the mechanical excitations using acoustic radiation force (ARF) impulses applied to the region of interest.

6. The method of claim 1, wherein the MRI system further encodes a position of an initial disturbance caused by the mechanical excitation in each phase image.

7. The method of claim 6, wherein the position of the initial disturbance and the propagating shear wavefront are encoded as positive and negative values in the phase image.

8. The method of claim 1, wherein the ultrasound transducer generates the mechanical excitations using a focused ultrasound (FUS) beam and lobes of the MEGs are oriented parallel to the FUS beam.

9. The method of claim 1, wherein the MRI system captures each phase image using a 3D gradient echo segmented echo planar imaging pulse sequence.

10. The method of claim 1, further comprising:
using velocity values in the plurality of shear wave velocity maps to determine one or more shear modulus values for the region of interest.

11. A system for mapping shear wave velocity in biological tissues, the system comprising:
an ultrasound transducer configured to generate mechanical excitations at a plurality of locations in a region of interest comprising generating a first mechanical excitation at a first origin location and a second mechanical excitation at a second origin location;
an MRI system configured to capture a phase image of each mechanical excitation, wherein multi-lobed motion encoding gradient (MEGs) of the MRI system encode a propagating shear wavefront caused by the mechanical excitation wherein the propagating shear wavefront is encoded at multiple propagation distances in the phase image, wherein the MEGs are trapezoidal shaped waveforms, wherein capturing the phase image of each mechanical excitation comprises:
capturing a first phase image of the first mechanical excitation, wherein the multi-lobed MEGs of the MRI system encode a first propagating shear wavefront caused by the first mechanical excitation wherein the first propagating shear wavefront is encoded at multiple propagation distances in the first phase image, and
capturing a second phase image of the second mechanical excitation, wherein the multi-lobed MEGs of the MRI system encode a second propagating shear wavefront caused by the second mechanical excitation wherein the second propagating shear wavefront is encoded at multiple propagation distances in the second phase image; and one or more computers configured to:
identify an overlapping area between a first encoded wavefront in the first phase image and a second encoded wavefront in the second phase image,
calculate a shear wave speed in the overlapping area,
measure a distance between the first origin location and the first encoded wavefront,
calculate a propagation time using the measured distance, wherein the propagation time is a time between the first mechanical excitation and the first encoded wavefront,
calculate a shear wave speed in the area between the first origin location and the first encoded wavefront using the propagation time and the measured distance, generate a plurality of shear wave velocity maps based on the phase images, wherein each shear wave velocity map depicts velocity between adjacent propagating shear wavefronts, and combine the plurality of shear wave speed values to generate a composite shear wave velocity map of the region of interest.

12. The system of claim 11, wherein:

the MRI system is further configured to receive a reference image of a region of interest without any mechanical excitation caused by the ultrasound transducer in the region of interest;

the computers are further configured to, prior to generation of the shear wave velocity maps, subtract the reference MRI image from each phase image to minimize phase variations not caused by the mechanical excitations.

13. A method for mapping shear wave velocity in biological tissues, the method comprising:

using an ultrasound transducer to generate mechanical excitations at a plurality of locations in a region of interest, wherein using the ultrasound transducer to generate mechanical excitations comprises:

using the ultrasound transducer to generate a first mechanical excitation at a first origin location, and using the ultrasound transducer to generate a second mechanical excitation;

using an MRI system to capture a phase image of each mechanical excitation, wherein multi-lobed motion encoding gradients (MEGs) of the MRI system encode a propagating shear wavefront caused by the mechanical excitation wherein the propagating shear wavefront is encoded at multiple propagation distances in the phase image, wherein using the MRI system to capture the phase image of each mechanical excitation comprises:

using the MRI system to capture a first phase image of the first mechanical excitation, wherein the MRI systems uses multi-lobed MEGs having a first shape to encode a first propagating shear wavefront caused by the first mechanical excitation wherein the first propagating shear wavefront is encoded at multiple propagation distances in the first phase image;

using the MRI system to capture a second phase image of the second mechanical excitation, wherein the MRI system uses multi-lobed MEGs having a second shape to encode a second propagating shear wavefront caused by the second mechanical excitation wherein the second propagating shear wavefront is encoded at multiple propagation distances in the second phase image;

generating a plurality of shear wave velocity maps based on the phase images, wherein each shear wave velocity map depicts velocity between adjacent propagating shear wavefronts;

combining a plurality of shear wave speed values to generate a composite shear wave velocity map of the region of interest; and calculating a shear wave speed in an area between the first origin location and a first wavefront position of the first propagating shear wavefront, wherein calculating the shear wave speed comprises:

generating a complex image by combining the first phase image and the second phase image, and calculating the shear wave speed using the complex image.

14. The method of claim 13, wherein the first shape is sinusoidal and the second shape is cosinusoidal.

15. The method of claim 13, wherein each phase image differs in relative timing of the mechanical excitations in the region of interest.

16. The method of claim 13, wherein the MEGs are sinusoidal shaped waveforms, the method further comprising:

calculating the shear wave speed in the area between the first origin location and the first wavefront position of the first propagating shear wavefront, wherein calculating the shear wave speed comprises:

generating the complex image by combining the first phase image and the second phase image, and calculating the shear wave speed using the complex image, wherein a time between the first mechanical excitation and when the MRI system begins encoding the first propagating shear wavefront is different than a time between the second mechanical excitation and when the MRI system begins encoding the second propagating shear wavefront.

17. The method of claim 16 wherein the multi-lobed MEGs encoding the second propagating shear wavefront are shifted by ¼ of a period of the multi-lobed MEGs encoding the first propagating shear wavefront.

18. A system for mapping shear wave velocity in biological tissues, the system comprising:

an ultrasound transducer configured to generate mechanical excitations at a plurality of locations in a region of interest comprising generating a first mechanical excitation at a first origin location and generating a second mechanical excitation;

an MRI system configured to capture a phase image of each mechanical excitation, wherein multi-lobed motion encoding gradients (MEGs) of the MRI system encode a propagating shear wavefront caused by the mechanical excitation wherein the propagating shear wavefront is encoded at multiple propagation distances in the phase image, wherein capturing the phase image of each mechanical excitation comprises:

using the MRI system to capture a first phase image of the first mechanical excitation, wherein the MRI system uses multi-lobed MEGs having a first shape to encode a first propagating shear wavefront caused by the first mechanical excitation wherein the first propagating shear wavefront is encoded at multiple propagation distances in the first phase image;

using the MRI system to capture a second phase image of the second mechanical excitation, wherein the MRI system uses multi-lobed MEGs having a second shape to encode a second propagating shear wavefront caused by the second mechanical excitation wherein the second propagating shear wavefront is encoded at multiple propagation distances in the second phase image; and one or more computers configured to:

generate a plurality of shear wave velocity maps based on the phase images, wherein each shear wave velocity map depicts velocity between adjacent propagating shear wavefronts, combine a plurality of shear wave speed values to generate a composite shear wave velocity map of the region of interest, and calculate a shear wave speed in an area between the first origin location and a first wavefront position of the first propagating shear wavefront, wherein calculating the shear wave speed comprises:
generating a complex image by combining the first phase image and the second phase image, and
calculating the shear wave speed using the complex image.

19. The system of claim 18, wherein the MEGs are sinusoidal shaped waveforms.

\* \* \* \* \*